US012315640B2

(12) United States Patent
Dohrmann et al.

(10) Patent No.: US 12,315,640 B2
(45) Date of Patent: May 27, 2025

(54) ATMOSPHERIC MIRRORING AND DYNAMICALLY VARYING THREE-DIMENSIONAL ASSISTANT ADDISON INTERFACE FOR INTERIOR ENVIRONMENTS

(71) Applicant: Electronic Caregiver, Inc., Las Cruces, NM (US)

(72) Inventors: Anthony Dohrmann, El Paso, TX (US); Roberto Abel Salcido, El Paso, TX (US); David W. Keeley, Frisco, TX (US); Samuel Blake, Las Cruces, NM (US); Madison Anne Markle, Las Cruces, NM (US); Sierra Danielle Guerrero, Las Cruces, NM (US); Taylor Allen Bunker, Las Cruces, NM (US); Judah Tveito, Las Cruces, NM (US)

(73) Assignee: Electronic Caregiver, Inc., Las Cruces, NM (US)

(*) Notice: Subject to any disclaimer, the term of this patent is extended or adjusted under 35 U.S.C. 154(b) by 156 days.

(21) Appl. No.: 17/844,614

(22) Filed: Jun. 20, 2022

(65) Prior Publication Data
US 2022/0319713 A1   Oct. 6, 2022

Related U.S. Application Data

(63) Continuation-in-part of application No. 17/735,750, filed on May 3, 2022, and a continuation-in-part of
(Continued)

(51) Int. Cl.
*G16H 50/30* (2018.01)
*G10L 15/22* (2006.01)
(Continued)

(52) U.S. Cl.
CPC ............. *G16H 50/30* (2018.01); *G10L 15/22* (2013.01); *G16H 40/60* (2018.01); *G16H 50/20* (2018.01); *G10L 2015/223* (2013.01)

(58) Field of Classification Search
None
See application file for complete search history.

(56) References Cited

U.S. PATENT DOCUMENTS 7,612,681 B2   11/2009   Azzaro et al.
7,971,141 B1    6/2011   Quinn et al.
(Continued)

FOREIGN PATENT DOCUMENTS

CA   2949449 A1   11/2015
CN   104361321 A   2/2015
(Continued)

OTHER PUBLICATIONS

Unity (game engine); Wikipedia website (Year: 2024).*
(Continued)

*Primary Examiner* — John A Pauls
(74) *Attorney, Agent, or Firm* — Carr & Ferrell LLP

(57) ABSTRACT

Exemplary embodiments include an intelligent secure networked health messaging system configured by at least one processor to execute instructions stored in memory, the system including a data retention system and a health analytics system, the health analytics system performing asynchronous processing with a patient's computing device and the health analytics system communicatively coupled to a deep neural network, a web services layer providing access to the data retention and the health analytics system, a batching service, wherein an application server layer transmits a request to the web services layer for data, the request processed by the batching service transparently to the patient, the request processed by the batching service trans-
(Continued)

parently to the patient such that the patient can continue to use a patient facing application without disruption, and the patient-facing application having an audio sensor and a computer video sensor.

20 Claims, 18 Drawing Sheets

Related U.S. Application Data application No. 17/693,151, filed on Mar. 11, 2022, now abandoned, and a continuation-in-part of application No. 17/013,357, filed on Sep. 4, 2020, now Pat. No. 12,011,259, said application No. 17/693,151 is a continuation-in-part of application No. 16/169,760, filed on Oct. 24, 2018, said application No. 17/013,357 is a continuation of application No. 15/530,185, filed on Dec. 9, 2016.

(60) Provisional application No. 63/213,625, filed on Jun. 22, 2021, provisional application No. 63/184,060, filed on May 4, 2021, provisional application No. 62/618,550, filed on Jan. 17, 2018, provisional application No. 62/386,768, filed on Dec. 11, 2015.

(51) Int. Cl.
*G16H 40/60* (2018.01)
*G16H 50/20* (2018.01)

(56) References Cited

U.S. PATENT DOCUMENTS

| | | |
|---|---|---|
| 8,206,325 B1 | 6/2012 | Najafi et al. |
| 8,771,206 B2 | 7/2014 | Gettelman et al. |
| 9,072,929 B1 | 7/2015 | Rush et al. |
| 9,972,187 B1 | 5/2018 | Srinivasan et al. |
| 10,387,963 B1 | 8/2019 | Leise et al. |
| 10,417,388 B2 | 9/2019 | Han et al. |
| 10,628,635 B1 | 4/2020 | Carpenter, II et al. |
| 10,761,691 B2 | 9/2020 | Anzures et al. |
| 10,813,572 B2 | 10/2020 | Dohrmann et al. |
| 10,943,407 B1 | 3/2021 | Morgan et al. |
| 10,998,101 B1 | 5/2021 | Tran et al. |
| 11,837,341 B1* | 12/2023 | Chandra S R ...... H04L 63/0428 |
| 12,009,083 B2 | 6/2024 | Keeley et al. |
| 12,011,259 B2 | 6/2024 | Dohrmann et al. |
| 12,265,900 B2 | 4/2025 | Dohrmann et al. |
| 2002/0062342 A1 | 5/2002 | Sidles |
| 2004/0109470 A1 | 6/2004 | Derechin et al. |
| 2004/0147817 A1* | 7/2004 | Dewing ................ G16H 50/20 |
| | | 128/923 |
| 2004/0189708 A1 | 9/2004 | Larcheveque |
| 2005/0035862 A1 | 2/2005 | Wildman et al. |
| 2007/0032929 A1 | 2/2007 | Yoshioka |
| 2008/0010293 A1 | 1/2008 | Zpevak et al. |
| 2008/0186189 A1 | 8/2008 | Azzaro et al. |
| 2009/0030945 A1 | 1/2009 | Miller et al. |
| 2009/0094285 A1 | 4/2009 | Mackle et al. |
| 2010/0124737 A1 | 5/2010 | Panzer |
| 2011/0112855 A1 | 5/2011 | Chen et al. |
| 2011/0126207 A1 | 5/2011 | Wipfel et al. |
| 2012/0025989 A1 | 2/2012 | Cuddihy et al. |
| 2012/0075464 A1 | 3/2012 | Derenne et al. |
| 2012/0165618 A1* | 6/2012 | Algoo ................ A61B 5/744 |
| | | 600/300 |
| 2012/0179067 A1 | 7/2012 | Wekell |
| 2012/0229634 A1 | 9/2012 | Laett et al. |
| 2013/0060167 A1 | 2/2013 | Dracup |
| 2013/0123667 A1 | 5/2013 | Komatireddy et al. |
| 2013/0127620 A1 | 5/2013 | Siebers et al. |
| 2013/0167025 A1 | 6/2013 | Patri et al. |
| 2013/0204545 A1 | 8/2013 | Solinsky |
| 2013/0212501 A1 | 8/2013 | Anderson et al. |
| 2013/0237395 A1 | 9/2013 | Hjelt et al. |
| 2013/0289449 A1 | 10/2013 | Stone et al. |
| 2013/0303860 A1 | 11/2013 | Bender et al. |
| 2014/0074454 A1 | 3/2014 | Brown et al. |
| 2014/0094136 A1* | 4/2014 | Huang ................ H04W 4/02 |
| | | 455/456.3 |
| 2014/0112321 A1 | 4/2014 | Larson et al. |
| 2014/0112351 A1* | 4/2014 | Furukawa ............... H04L 69/22 |
| | | 370/465 |
| 2014/0148733 A1 | 5/2014 | Stone et al. |
| 2014/0214441 A1 | 7/2014 | Young et al. |
| 2014/0232600 A1 | 8/2014 | Larose et al. |
| 2014/0243686 A1 | 8/2014 | Kimmel |
| 2014/0278605 A1 | 9/2014 | Borucki et al. |
| 2014/0317502 A1 | 10/2014 | Brown et al. |
| 2014/0337048 A1 | 11/2014 | Brown et al. |
| 2014/0343460 A1 | 11/2014 | Evans, III et al. |
| 2015/0005674 A1 | 1/2015 | Schindler |
| 2015/0109442 A1 | 4/2015 | Derenne et al. |
| 2015/0359467 A1 | 12/2015 | Tran |
| 2016/0037057 A1 | 2/2016 | Westin et al. |
| 2016/0125620 A1 | 5/2016 | Heinrich et al. |
| 2016/0154977 A1 | 6/2016 | Jagadish et al. |
| 2016/0156696 A1* | 6/2016 | Liddicott ................ H04L 67/06 |
| | | 709/203 |
| 2016/0216770 A1 | 7/2016 | Jang et al. |
| 2016/0267699 A1 | 9/2016 | Borke et al. |
| 2017/0055917 A1 | 3/2017 | Stone et al. |
| 2017/0147154 A1 | 5/2017 | Steiner et al. |
| 2017/0189751 A1 | 7/2017 | Knickerbocker et al. |
| 2017/0192950 A1 | 7/2017 | Gaither et al. |
| 2017/0197115 A1 | 7/2017 | Cook et al. |
| 2017/0223176 A1 | 8/2017 | Anzures et al. |
| 2017/0251985 A1 | 9/2017 | Newton |
| 2017/0336933 A1 | 11/2017 | Hassel |
| 2017/0337274 A1 | 11/2017 | Ly et al. |
| 2018/0005448 A1 | 1/2018 | Choukroun et al. |
| 2018/0096504 A1 | 4/2018 | Valdivia et al. |
| 2018/0189756 A1 | 7/2018 | Purves et al. |
| 2018/0330810 A1 | 11/2018 | Gamarnik et al. |
| 2018/0360349 A9 | 12/2018 | Dohrmann et al. |
| 2018/0365383 A1 | 12/2018 | Bates |
| 2018/0365759 A1 | 12/2018 | Balzer et al. |
| 2019/0019573 A1 | 1/2019 | Lake et al. |
| 2019/0019582 A1 | 1/2019 | Wallis et al. |
| 2019/0116212 A1 | 4/2019 | Spinella-Mamo |
| 2019/0156575 A1 | 5/2019 | Korhonen |
| 2019/0176043 A1 | 6/2019 | Gosine et al. |
| 2019/0220727 A1 | 7/2019 | Dohrmann et al. |
| 2019/0259475 A1 | 8/2019 | Dohrmann et al. |
| 2020/0043594 A1 | 2/2020 | Miller et al. |
| 2020/0066391 A1 | 2/2020 | Sachdeva |
| 2020/0129107 A1 | 4/2020 | Sharma et al. |
| 2020/0236090 A1 | 7/2020 | De Beer et al. |
| 2021/0007631 A1 | 1/2021 | Dohrmann et al. |
| 2021/0016150 A1 | 1/2021 | Jeong et al. |
| 2021/0052230 A1 | 2/2021 | Roh |
| 2021/0110894 A1 | 4/2021 | Shriberg et al. |
| 2021/0134456 A1 | 5/2021 | Posnack et al. |
| 2021/0375426 A1 | 12/2021 | Gobezie et al. |
| 2022/0031199 A1 | 2/2022 | Hao et al. |
| 2022/0157427 A1 | 5/2022 | Keeley et al. |
| 2022/0199252 A1 | 6/2022 | Dohrmann et al. |
| 2022/0319696 A1 | 10/2022 | Dohrmann et al. |
| 2022/0319714 A1 | 10/2022 | Dohrmann et al. |
| 2022/0359091 A1 | 11/2022 | Dohrmann et al. |
| 2023/0108601 A1 | 4/2023 | Coelho Alves et al. |

FOREIGN PATENT DOCUMENTS

| | | |
|---|---|---|
| CN | 106056035 A | 10/2016 |
| CN | 106940692 A | 7/2017 |
| CN | 107411515 A | 12/2017 |
| EP | 3703009 A1 | 9/2020 |
| JP | 2000232963 A | 8/2000 |
| JP | 2002304362 A | 10/2002 |
| JP | 2005228305 A | 8/2005 |
| JP | 2008062071 A | 3/2008 |

(56) References Cited

FOREIGN PATENT DOCUMENTS

| JP | 2008123318 A | 5/2008 |
|---|---|---|
| JP | 2008229266 A | 10/2008 |
| JP | 2016525383 A | 8/2016 |
| JP | 2017187914 A | 10/2017 |
| KR | 20170069501 A | 6/2017 |
| WO | WO2000005639 A2 | 2/2000 |
| WO | WO2014210344 A1 | 12/2014 |

OTHER PUBLICATIONS

Leber, Jessica, "The Avatar Will See You Now", MIT Technology Review, Sep. 17, 2013, 4 pages.

Marston et al., "The design of a purpose-built exergame for fall prediction and prevention for older people", European Review of Aging and Physical Activity 12:13, <URL:https://eurapa.biomedcentral.com/track/pdf/10.1186/s11556-015-0157-4.pdf>, Dec. 8, 2015, 12 pages.

Ejupi et al., "Kinect-Based Five-Times-Sit-to-Stand Test for Clinical and In-Home Assessment of Fall Risk in Older People", Gerontology (vol. 62), (2015-05-28), <URL:https://www.karger.com/Article/PDF/381804>, May 28, 2015, 7 pages.

Festl et al., "iStoppFalls: A Tutorial Concept and prototype Contents", <URL:https://hcisiegen.de/wp-uploads/2014/05/isCtutorialdoku.pdf>, Mar. 30, 2013, 36 pages.

Dubois et al., "A Gait Analysis Method Based on a Depth Camera for Fall Prevention," Proc. of the 36th Annual International Conference of the IEEE Engineering in Medicine and Biology Society (EMBS), Aug. 30, 2014, pp. 4515-4518 (Abstract only).

Marston et al., "The design of a purpose-built exergame for fall prediction and prevention for older people," European Review of Aging and Physical Activity, Dec. 8, 2015, vol. 12, pp. 1-12.

Wasenmuller et al., "Comparison of Kinect V1 and V2 Depth Images in Terms of Accuracy and Precision", Computer Vision—ACCV 2016 Workshops (Taipei, Taiwan, Nov. 20-24, 2016), Revised Selected Papers, Part II, Mar. 16, 2017 (Mar. 16, 2017), XP055942856, DOI: 10.1007/978-3-319-54427-4, ISBN: 978-3-319-54427-4 Retrieved from the Internet: URL: https://link.springer.com/content/pdf/10.1007/978-3-319-54427-4_3.pdf>, pp. 1-12.

Stone et al., "Evaluation of an Inexpesive Depth Camera for In-Home Gait Assessment," Journal of Ambient Intelligence and Smart Environments Jan. 2011 3(4); pp. 349-361.

Similan et al., Gait analysis and estimation of changes in fall risk factors, 2015 37th Annual International Conference of the IEEE Engineering in Medicine and Biology Society (EMBC), Milan, Italy, 2015, doi: 10.1109/EMBC 2015.7319988 (abstract only); 3 pages.

\* cited by examiner

Order entry specifications.

1. User first and last name:
2. Likes to be called:
3. User address of system:
4. User age:
5. User gender:
6. What is your current gender identity? (Check ALL that apply)
7. Gait code
8. Lock box yes or now
9. Lock box location
10. Lock box code
11. User billing name and address if different
12. Primary telephone contact number (premises landline or cellular)
13. Secondary telephone contact name
14. Secondary telephone
15. Name of primary physician
16. Preferred hospital
17. Known allergies
18. Known health conditions with table of conditions check yes or no
19. Special health requirements or other conditions- fill in notation fields:
- Medication reminder #1 Mon-Sunday and timetables
- Medication type instructions enter here _____
- Medication reminder #2 Mon-Sunday and timetables
- Medication type instructions enter here _____
- Medication reminder #3 Mon-Sunday and timetables
- Medication type instructions enter here _____
- Medication reminder #4 Mon-Sunday and timetables
- Medication type instructions enter here _____
- Medication reminder #5 Mon-Sunday and timetables
- Medication type instructions enter here _____
- Medication reminder #6 Mon-Sunday and timetables
- Medication type instructions enter here _____
- Medication reminder #7 Mon-Sunday and timetables
- Medication type instructions enter here _____
- Medication reminder #8 Mon-Sunday and timetables
- Medication type instructions enter here _____
- Medication reminder #9 Mon-Sunday and timetables
- Medication type instructions enter here _____
- Medication reminder #10 Mon-Sunday and timetables
- Medication type instructions enter here _____
- Medication reminder #11 Mon-Sunday and timetables
- Medication type instructions enter here _____
- Medication reminder #12 Mon-Sunday and timetables
- Medication type instructions enter here _____
- Medication reminder #13 Mon-Sunday and timetables
- Medication type instructions enter here _____
- Medication reminder #14 Mon-Sunday and timetables
- Medication type instructions enter here _____

FIG. 13A

- Medication reminder #15 Mon-Sunday and timetables
- Medication type instructions enter here _____
- Medication reminder #16 Mon-Sunday and timetables
- Medication type instructions enter here _____
- Medication reminder #17 Mon-Sunday and timetables
- Medication type instructions enter here _____
- Medication reminder #18 Mon-Sunday and timetables

- Vitals reminder #1 Mon-Sunday and timetables
  Vitals type instructions enter here _____
- Vitals reminder #2 Mon-Sunday and timetables
- Vitals type instructions enter here _____
- Vitals reminder #3 Mon-Sunday and timetables
- Vitals type instructions enter here _____
- Vitals reminder #4 Mon-Sunday and timetables
- Vitals type instructions enter here _____
- Vitals type instructions enter here _____
- Vitals reminder #5 Mon-Sunday and timetables
- Vitals type instructions enter here _____
- Vitals reminder #6 Mon-Sunday and timetables
- Vitals type instructions enter here _____
- Vitals reminder #7 Mon-Sunday and timetables
- Vitals type instructions enter here _____
- Vitals reminder #8 Mon-Sunday and timetables
- Vitals type instructions enter here _____
- Vitals reminder #9 Mon-Sunday and timetables
- Vitals type instructions enter here _____
- Vitals reminder #10 Mon-Sunday and timetables
- Vitals type instructions enter here _____
- Vitals reminder #11 Mon-Sunday and timetables
- Vitals type instructions enter here _____
- Vitals reminder #12 Mon-Sunday and timetables
- Vitals type instructions enter here _____
- Vitals reminder #13 Mon-Sunday and timetables
  Vitals type instructions enter here _____
- Vitals reminder #14 Mon-Sunday and timetables
- Vitals type instructions enter here _____
- Vitals reminder #15 Mon-Sunday and timetables
- Vitals type instructions enter here _____
- Vitals reminder #16 Mon-Sunday and timetables
- Vitals type instructions enter here _____
- Vitals type instructions enter here _____
- Vitals reminder #17 Mon-Sunday and timetables
- Vitals type instructions enter here _____
- Vitals reminder #18 Mon-Sunday and timetables
- Vitals type instructions enter here _____
- Vitals reminder #19 Mon-Sunday and timetables
- Vitals type instructions enter here _____
- Vitals reminder #20 Mon-Sunday and timetables

FIG. 13B

- Vitals type instructions enter here _____
- Vitals reminder #21 Mon-Sunday and timetables
- Vitals type instructions enter here _____
- Vitals reminder #22 Mon-Sunday and timetables
- Vitals type instructions enter here _____
- Vitals reminder #23 Mon-Sunday and timetables
- Vitals type instructions enter here _____
- Vitals reminder #24 Mon-Sunday and timetables
- Vitals type instructions enter here _____

- Hydration reminder instructions enter here _____
- Hydration reminder #1 Mon-Sunday and timetables
- Hydration reminder instructions enter here _____
- Hydration reminder #2 Mon-Sunday and timetables
- Hydration reminder instructions enter here _____
- Hydration reminder #3 Mon-Sunday and timetables
Hydration reminder instructions enter here _____

- Hydration reminder #4 Mon-Sunday and timetables
- Hydration reminder instructions enter here _____
- Hydration reminder #5 Mon-Sunday and timetables
- Hydration reminder instructions enter here _____
- Hydration reminder #6 Mon-Sunday and timetables
- Hydration reminder instructions enter here _____
- Hydration reminder #7 Mon-Sunday and timetables
- Hydration reminder instructions enter here _____
- Hydration reminder #8 Mon-Sunday and timetables
- Hydration reminder instructions enter here _____
- Hydration reminder #9 Mon-Sunday and timetables
- Hydration reminder instructions enter here _____
- Hydration reminder #10 Mon-Sunday and timetables
- Hydration reminder instructions enter here _____
- Hydration reminder #11 Mon-Sunday and timetables
- Hydration reminder instructions enter here _____
- Hydration reminder #12 Mon-Sunday and timetables

- Nutrition reminder instructions enter here _____
- Nutrition reminder #1 Mon-Sunday and timetables
- Nutrition reminder instructions enter here _____
- Nutrition reminder #2 Mon-Sunday and timetables
- Nutrition reminder instructions enter here _____
- Nutrition reminder #3 Mon-Sunday and timetables
- Nutrition reminder instructions enter here _____
- Nutrition reminder #4 Mon-Sunday and timetables
- Nutrition reminder instructions enter here _____
- Nutrition reminder #5 Mon-Sunday and timetables
- Nutrition reminder instructions enter here _____
- Nutrition reminder #6 Mon-Sunday and timetables

FIG. 13C

- Nutrition reminder instructions enter here _____
- Nutrition reminder #7 Mon-Sunday and timetables
- Nutrition reminder instructions enter here _____
- Nutrition reminder #8 Mon-Sunday and timetables
- Nutrition reminder instructions enter here _____
- Nutrition reminder #9 Mon-Sunday and timetables
- Nutrition reminder instructions enter here _____
- Nutrition reminder #10 Mon-Sunday and timetables
- Nutrition reminder instructions enter here _____
- Nutrition reminder #11 Mon-Sunday and timetables
- Nutrition reminder instructions enter here _____
- Nutrition reminder #12 Mon-Sunday and timetables

- A.M. Activity Monitoring between the hours of _____ a.m. and _____ a.m. (min 1- max 10 hours)
- P.M. Activity Monitoring between the hours of _____ p.m. and _____ p.m. (min 1- max 10 hours)

- Health survey question #1 text _____ and timetables
- Health survey question #2 text _____ and timetables
- Health survey question #3 text _____ and timetables
- Health survey question #4 text _____ and timetables
- Health survey question #5 text _____ and timetables
- Health survey question #6 text _____ and timetables
- Health survey question #7 text _____ and timetables
- Health survey question #8 text _____ and timetables
- Health survey question #9 text _____ and timetables
- Health survey question #10 text _____ and timetables
- Health survey question #11 text _____ and timetables
- Health survey question #12 text _____ and timetables
- Health survey question #13 text _____ and timetables
- Health survey question #14 text _____ and timetables
- Health survey question #15 text _____ and timetables
- Health survey question #16 text _____ and timetables
- Health survey question #17 text _____ and timetables
- Health survey question #18 text _____ and timetables
- Health survey question #19 text _____ and timetables
- Health survey question #20 text _____ and timetables
- Health survey question #21 text _____ and timetables
- Health survey question #22 text _____ and timetables
- Health survey question #23 text _____ and timetables
- Health survey question #24 text _____ and timetables

Behavioral health survey _____ yes or no

Behavioral health survey timetables (each has a question and a response that reports to dashboard)

FIG. 13D

- General reminder #1 text_____ and timetables
- General reminder #2 text_____ and timetables
- General reminder #3 text_____ and timetables
- General reminder #4 text_____ and timetables
- General reminder #5 text_____ and timetables
- General reminder #6 text_____ and timetables
- General reminder #7 text_____ and timetables
- General reminder #8 text_____ and timetables
- General reminder #9 text_____ and timetables
- General reminder #10 text_____ and timetables
- General reminder #11 text_____ and timetables
- General reminder #12 text_____ and timetables

- Number of repeat reminders before reporting alert to central station _____ default 3/selectable 2-5
- Duration of alert annunciation _____ default 2 min/selectable from 1-5 minutes
- Number of snooze cycles allowed for reminder alerts _____ default 3/selectable 3-5
- Duration of snooze cycle _____ default 15 minutes/selectable 5-120 minutes
- Mediation consumption feature? Yes/No
- Adverse drug reaction inquiries? Yes/No
- Body temperature device Yes/No

- Blood pressure device yes/no  small____ medium____ large____
  Threshold alert if higher than _____ If lower than_____
- Glucose meter yes/no
  Threshold alert if higher than _____ If lower than_____
- Spirometer yes/no
  Threshold alert if higher than _____ If lower than_____
- Pulse Oximeter yes/no

Threshold alert if higher than _____ If lower than_____

Physical Therapy

PT timetables. Each should have a drop-down menu to select from a menu of MOCAP recorded demonstration routines. Demonstration routines may be presented for left and right.

- PT reminder #1 text_____ repetitions _____and timetables
- PT reminder #2 text_____ repetitions _____and timetables
- PT reminder #3 text_____ repetitions _____and timetables
- PT reminder #4 text_____ repetitions _____and timetables
- PT reminder #5 text_____ repetitions _____and timetables
- PT reminder #6 text_____ repetitions _____and timetables
- PT reminder #7 text_____ repetitions _____and timetables
- PT reminder #8 text_____ repetitions _____and timetables
- PT reminder #9 text_____ repetitions _____and timetables
- PT reminder #10 text_____ repetitions _____and timetables

FIG. 13E

- Emergency pendant yes/no #_____
- Special instructions for notification or response- fill in field
- Remote Patient Monitoring Patient yes or no
- Servicing RPM agency name and telephone number
- Local first responders name and number _____
- Private ambulance company? ___ Yes or no
- Private ambulance company name and number_____ #_____
- Emergency response service yes or no _____

- Responsible Notification Party #1 Name_____ Ph#1 _____ Cell #_____ Email_____ Relation to party_____ Priority level___ 1-5
- Responsible Notification Party #2 Name_____ Ph#1 _____ Cell #_____ Email_____ Relation to party_____ Priority level___ 1-5
- Responsible Notification Party #3 Name_____ Ph#1 _____ Cell #_____ Email_____ Relation to party_____ Priority level___ 1-5
- Responsible Notification Party #4 Name_____ Ph#1 _____ Cell #_____ Email_____ Relation to party_____ Priority level___ 1-5
- Responsible Notification Party #5 Name_____ Ph#1 _____ Cell #_____ Email_____ Relation to party_____ Priority level___ 1-5

- Number of Addison consoles _____
- Number of Addison consoles with visual sensor _____
- Number of Remote Visual Sensors _____
- Payment information CC#, ACH or Invoice yes or no
- Billing date to begin ___ - ___ - _____
- Monthly fee $_____
- Equipment and installation fee $_____
- Desired installation day ___ - ___ - ___ at ___:___ a.m./p.m.

FIG. 13F

ATMOSPHERIC MIRRORING AND DYNAMICALLY VARYING THREE-DIMENSIONAL ASSISTANT ADDISON INTERFACE FOR INTERIOR ENVIRONMENTS

CROSS-REFERENCE TO RELATED APPLICATIONS

This Non-Provisional Patent Application claims the priority benefit of U.S. Provisional Application Ser. No. 63/213,625, filed on Jun. 22, 2021, titled "Atmospheric Mirroring and Dynamically Varying Three-Dimensional Assistant Addison Interface." The present application is a continuation-in-part of U.S. Non-Provisional patent application Ser. No. 17/735,750, filed on May 3, 2022, titled "Clinical Pathway Integration and Clinical Decision Support," which claims the priority benefit of U.S. Provisional Patent Application Ser. No. 63/184,060 filed on May 4, 2021, titled, "Clinical Pathway Integration and Clinical Decision Support." The present application is a continuation-in-part of U.S. Non-Provisional patent application Ser. No. 17/693,151, filed on Mar. 11, 2022, titled "Intelligent Secure Networked Health Messaging Systems and Methods," which is a continuation-in-part application that claims the priority benefit of U.S. Non-Provisional patent application Ser. No. 16/169,760 filed on Oct. 24, 2018 titled, "Computing Devices with Improved Interactive Animated Conversational Interface Systems," which in turn claims the priority benefit of U.S. Provisional Patent Application Ser. No. 62/618,550 filed on Jan. 17, 2018 titled, "Interactive Animated Conversational Interface System." The present application is a continuation-in-part of U.S. Non-Provisional patent application Ser. No. 17/013,357 filed on Sep. 4, 2020, titled "Systems and Methods for Fall Detection," which is a continuation of U.S. Non-Provisional patent application Ser. No. 15/530,185 filed on Dec. 9, 2016, titled "Intelligent System for Multi-Function Electronic Caregiving to Facilitate Advanced Health Diagnosis, Health Monitoring, Fall and Injury Prediction, Health Maintenance and Support, and Emergency Response," which in turn claims the priority benefit of U.S. Provisional Patent Application Ser. No. 62/386,768, filed on Dec. 11, 2015, titled "Intelligent System for Multi-Function Electronic Caregiving to Facilitate Advanced Health Diagnosis, Health Monitoring, Fall and Injury Prediction, Health Maintenance and Support, and Emergency Response." The present application is related to U.S. Non-Provisional application Ser. No. 17/844,619 filed concurrently herewith and titled "Atmospheric Mirroring and Dynamically Varying Three-Dimensional Assistant Addison Interface for External Environments," and the present application is related to U.S. Non-Provisional application Ser. No. 17/844,618 filed concurrently herewith and titled "Atmospheric Mirroring and Dynamically Varying Three-Dimensional Assistant Addison Interface for Behavioral Environments." The disclosures and appendices of all of the above applications are hereby incorporated by reference in their entireties.

FIELD OF INVENTION

The present technology relates generally to secure health messaging, and more particularly, but not by limitation, to systems and methods for secure health messaging that allow modular subsystem isolation, as well as latency remediation and improved user experiences.

SUMMARY

Exemplary embodiments include an intelligent secure networked health messaging system configured by at least one processor to execute instructions stored in memory, the system including a data retention system and a health analytics system, the health analytics system performing asynchronous processing with a patient's computing device and the health analytics system communicatively coupled to a deep neural network, a web services layer providing access to the data retention and the health analytics system, a batching service, wherein an application server layer transmits a request to the web services layer for data, the request processed by the batching service transparently to the patient, the request processed by the batching service transparently to the patient such that the patient can continue to use a patient facing application without disruption, the patient-facing application having an audio sensor and a computer video sensor, the application server layer including a high speed data corridor established between the application server layer and the patient's computing device that provides the patient-facing application that accesses the data retention and the health analytics system and the deep neural network through the web services layer that performs processing based on patient interaction with the patient-facing application, the patient-facing application configured to execute instructions including transmitting an interactive conversational patient interface to the patient's computing device with the deep neural network configured to receive a first input at an input layer, process the first input at one or more hidden layers, generate a first output, transmit the first output to an output layer, provide the first output to the patient-facing application, and provide the first output to the interactive conversational patient interface, the patient-facing application with the interactive conversational patient interface converting response data received by the patient's computing device into an audio file using a cloud-based text-to-speech application capable of being integrated into a web browser based avatar, the avatar being displayed on a display screen within the web browser of the patient's computing device as a three-dimensional electronic image of a human caregiver for a human patient, further comprising the three-dimensional electronic image of the human caregiver providing step-by-step verbal healthcare instructions to the human patient, monitoring a response from the human patient, and providing healthcare advice to the human patient based on the response.

The intelligent secure networked health messaging system, according to various exemplary embodiments, further includes the first output generating a first outcome, the first outcome being transmitted to the input layer, processing the first outcome by the one or more hidden layers, generating a second output, transmitting the second output to the output layer, providing the second output to the patient-facing application and the second output generating a second outcome. Additionally, the second outcome may be transmitted to the input layer and the output may include any of a clinically relevant care plan, a reminder, an alert, or a survey. The outcome may include any of a biometric parameter, a biometric parameter out of a predetermined threshold, a response to a survey, medication compliance information, an indicator of daily activity, an indicator of mood, or an indicator of stress. The processing by the one or more hidden layers may include using voice, speech, and computer video inputs to analyze signs of changes in health and behavioral status including but not limited to stress, anger, change in speech cadence, slurred speech or coughing. The processing may include determining changes in health and behavioral status including but not limited to anger, substance use, lack of sleep, stress, early onset of dementia or Alzheimer's disease, an adverse reaction to a medication, a stroke, Parkinson's disease, an increased risk of falling, or a lack of balance.

According to many exemplary embodiments, the interactive conversational user interface may be configured to mirror an interior environment, the mirrored interior environment including a realistic depiction of a fireplace that turns on when a temperature is below a certain threshold, a depiction of the patient's favorite color on an item in the patient's home, a depiction of the patient's favorite art style on an item in the patient's home, a depiction of holiday and religious celebration items in the patient's home, a depiction of the patient's favorite animals or pets in the patient's home, a depiction of interactable objects that respond when touched in the patient's home, a depiction of interactable objects including any of a piano, radio, bird feeder, plant, animal, wind chime, teacup, or vase that responds when touched in the patient's home, a depiction of interactable objects including a book that can be opened and read via touch or voice, a depiction of a patient's hobby in the patient's home, a depiction of a patient's hobby in the patient's home, the hobby being skiing and/or a depiction of a patient's hobby in the patient's home, the hobby being snowboarding.

DESCRIPTION OF THE DRAWINGS

Certain embodiments of the present technology are illustrated by the accompanying figures. It will be understood that the figures are not necessarily to scale. It will be understood that the technology is not necessarily limited to the particular embodiments illustrated herein.

FIGS. 13A-13F show examples of order entry specifications.

DETAILED DESCRIPTION

The detailed embodiments of the present technology are disclosed here. It should be understood, that the disclosed embodiments are merely exemplary of the technology, which may be embodied in multiple forms. Those details disclosed herein are not to be interpreted in any form as limiting, but as the basis for the claims.

Figure 1:
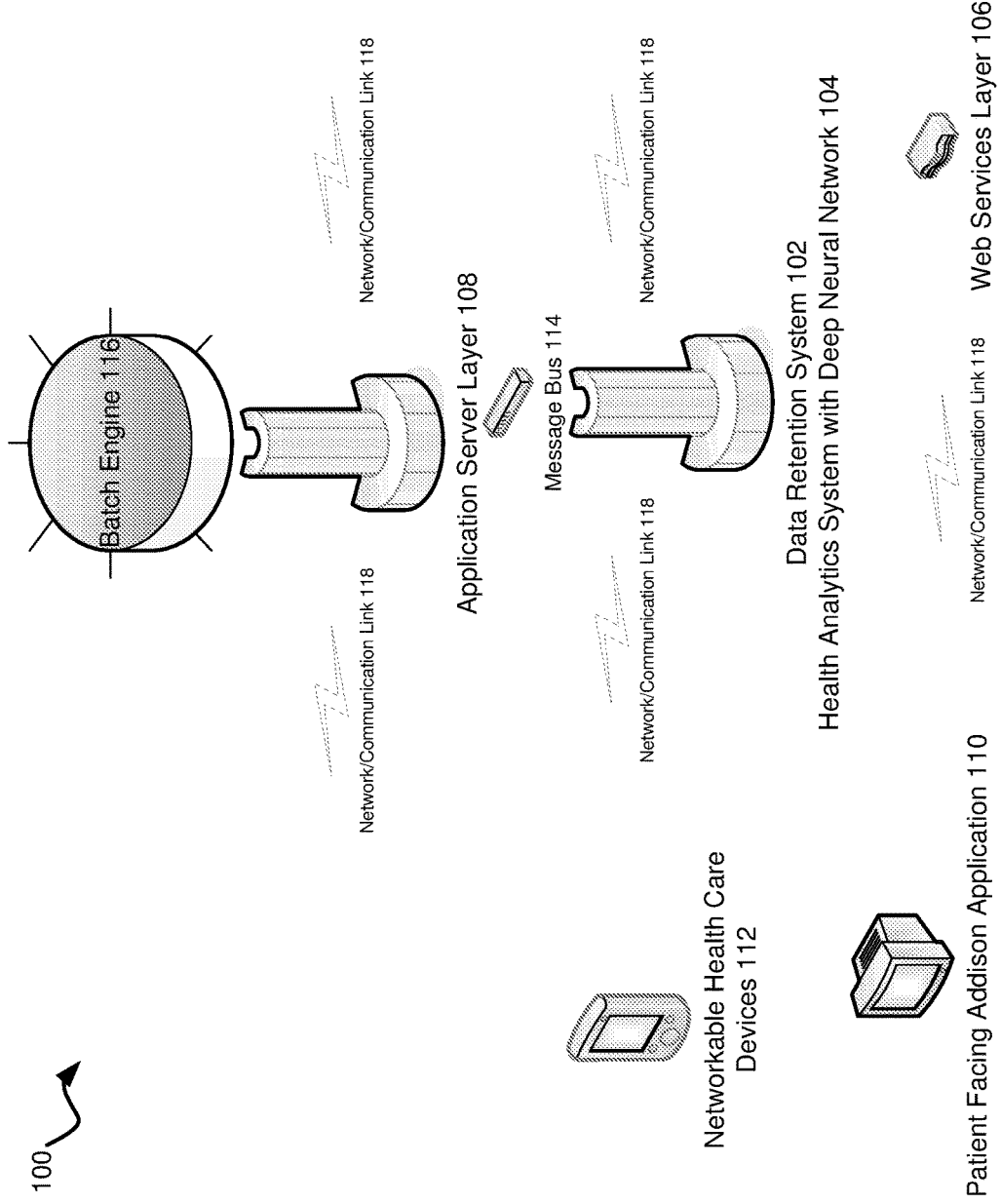
FIG. 1 is a schematic diagram of an exemplary computing architecture that includes a system constructed in accordance with the present disclosure.

FIG. 1 is a schematic diagram of an example secure health messaging system (hereinafter system 100) for practicing aspects of the present disclosure. The system 100 comprises a data retention system 102, a health analytics system with a deep neural network 104, a web services layer 106, and an application server layer 108 that provides, for example, modeling. Some or all of the activities occur over one or more network/communication links 118, and may occur in a cloud computing system and/or in an edge computing system.

In some embodiments, the data retention system 102 and the health analytics system with a deep neural network 104 are in secure isolation from a remainder of the secure messaging system 100 through a security protocol or layer. The data retention system 102 can also provide additional services such as logic, data analysis, risk model analysis, security, data privacy controls, data access controls, disaster recovery for data and web services—just to name a few.

The web services layer 106 generally provides access to the data retention system 102. According to some embodiments, the application server layer 108 is configured to provide a patient or user-facing Addison application 110 that accesses the data retention system 102 and the health analytics system with a deep neural network 104 through the web services layer 106.

In one or more embodiments, the application server layer 108 performs asynchronous processing based on user interaction with a health messaging application that processes data from a user via the patient-facing Addison application 110. A health messaging application can reside and execute on the application server layer 108. In other embodiments, the health messaging application may reside with the health analytics system with a deep neural network 104. In another embodiment, the health messaging application can be a client-side, downloadable application. Networkable health care devices 112, according to exemplary embodiments, may include a blood pressure monitor, glucometer, pro health hub, pulse oximeter, various sensors, including third party sensors, motion sensors, fall detection sensors, pressure sensors, telemetry sources, user behavior sources, and/or a thermometer. These devices may transmit information over a network, such as the Internet, to the system 100.

The systems of the present disclosure may implement security features that involve the use of multiple security tokens to provide security in the system 100. Security tokens are used between the web services layer 106 and application server layer 108.

In some embodiments, the system 100 implements an architected message bus 114. Rather than performing the refresh, which could involve data intensive and/or compute or operational intensive procedures by the system 100, the message bus 114 allows the request for refresh to be processed asynchronously by a batching process and provides a means for allowing the patient-facing Addison application to provide a view to the patient, allowing the patient to continue to access data without waiting on the system 100 to complete its refresh.

Also, latency can be remediated at the patient-facing Addison application 110 based on the manner in which the patient-facing Addison application 110 is created, how the data is displayed through the patient-facing Addison application 110 and how the data is stored and updated. For example, data displayed on the patient-facing Addison application 110 that changes frequently can cause frequent and unwanted refreshing of the entire patient-facing application and interactive graphical patient (or user) interfaces ("GUIs"). The present disclosure provides a solution to this issue by separating what is displayed on the GUI from the actual underlying data. The underlying data displayed on the GUI of the patient-facing Addison application 110 can be updated, as needed, on a segment-by-segment basis (could be defined as a zone of pixels on the display) at a granular level, rather than updating the entire GUI. That is, the GUI that renders the underlying data is programmatically separate from the underlying data cached by the client (e.g., device rendering the GUIs of the patient-facing Addison application 110). Due to this separation, when data being displayed on the GUI changes, re-rendering of the data is performed at a granular level, rather than at the page level. This process represents another example solution that remedies latency and improves user experiences with the patient-facing Addison application 110.

To facilitate these features, the patient-facing Addison application 110 will listen on the message bus 114 for an acknowledgement or other confirmation that the background processes to update the user account and/or the patient-facing Addison application have been completed by the application server layer 108. The patient-facing Addison application (or even part thereof) is updated as the system 100 completes its processing. This allows the patient-facing Addison application 110 to be usable, but the heavy lifting is being done transparently to the user by the application server layer 108. In sum, these features prevent or reduce latency issues even when an application provided through the patient-facing Addison application 110 is "busy." For example, a re-balance request is executed transparently by the application server layer 108 and batch engine 116. This type of transparent computing behavior by the system 100 allows for asynchronous operation (initiated from the application server layer 108 or message bus 114).

In some embodiments, a batch engine 116 is included in the system 100 and works in the background to process re-balance requests and coordinate a number of services. An example re-balance request would include an instance where a user selectively makes a data request. The batch engine 116 will transparently orchestrate the necessary operations required by the application server layer.

According to some embodiments, the batch engine 116 is configured to process requests transparently to a user so that the user can continue to use the user-facing Addison application 110 without disruption. For example, this transparent processing can occur when the application server layer 108 transmits a request to the web services layer 106 for data, and a time required for updating or retrieving the data meets or exceeds a threshold. For example, the threshold might specify that if the request will take more than five seconds to complete, then the batch engine 116 can process the request transparently. The selected threshold can be system configured.

In some embodiments, security of data transmission through the system 100 is improved by use of multiple security tokens. In one embodiment, a security protocol or security token is utilized between the application server layer 108 and the web services layer 106.

For example, feedback responses as described herein may be transmitted back to the data retention system 102 and/or the health analytics system with a deep neural network 104.

Figure 2:
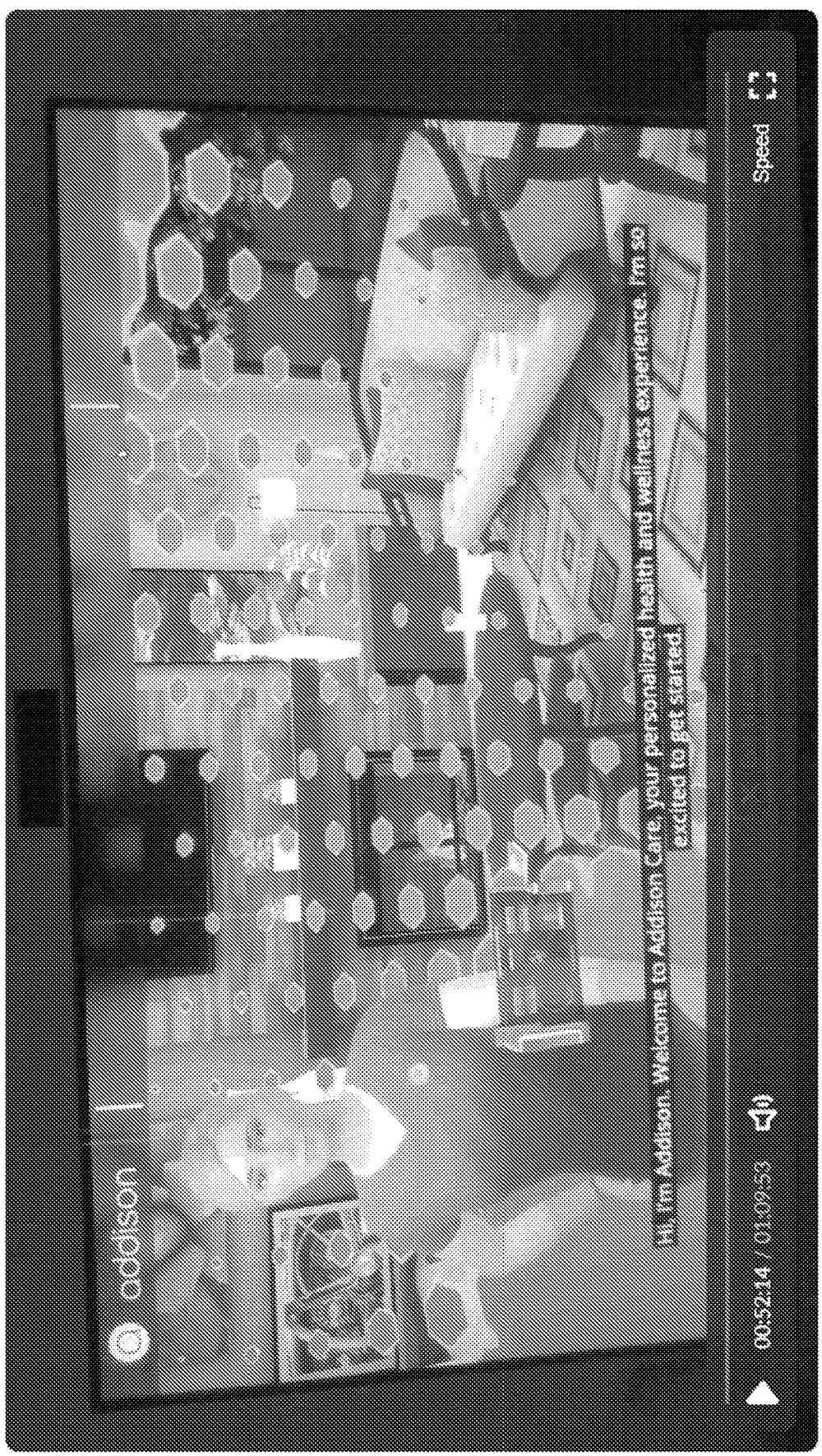
FIG. 2 shows an exemplary interactive conversational user interface.

FIG. 2 shows an exemplary interactive conversational user interface.

In some exemplary embodiments, the patient-facing Addison application 110 (FIG. 1) optionally utilizes Unity's eponymous platform. It is used to create two-dimensional, three-dimensional, virtual reality, and augmented reality video games and other simulations. It offers much more flexibility than a browser-based system. In some exemplary embodiments, Unity can be used to make "digital twins"—virtual copies of real-life objects, environments, and people. Unity can be used to create a non-player character or "NPC." An NPC is any character (such as in a game) that is not controlled by a player. For example, it applies to characters controlled by a gamemaster or referee rather than by another player. Unity also utilizes artificial intelligence tools in its virtual environments. With a digital twin, Unity can collect synthetic data off the simulation to advance its in-real-life ("IRL") twin. Additionally, in various exemplary embodiments, systems may be plugged into Unity, including facial recognition data, location data, CAD data, computer vision data, natural language processing data, blood pressure monitor data, glucometer data, pro health hub data, pulse oximeter data and/or thermometer data. As described and illustrated herein, in many exemplary embodiments, Addison may represent a NPC of an IRL caregiver (or vice versa). Further, Addison may be controlled in part by a patient or other human.

In some exemplary embodiments, the system 100 includes an Emergency Medical System and/or an Emergency Medical Technician module so emergency personnel can immediately access health care information either on site and/or over a network. The system 100 may also be configured to receive and store a Do Not Resuscitate ("DNR") order and/or a Last Will and Testament, etc.

The system 100 may also be configured with Addison having the ability to track inventories, such as groceries or medicines, and place automatic reorders. The system 100 may be configured with Addison having the ability to order food through various applications or goods or services through vendors such as Amazon®.

In various exemplary embodiments, the system 100 may be configured with facial recognition capabilities for Addison to determine and interpret a patient's face and changes, including mood and/or possible signs of a stroke or cardiovascular event.

Figure 3:
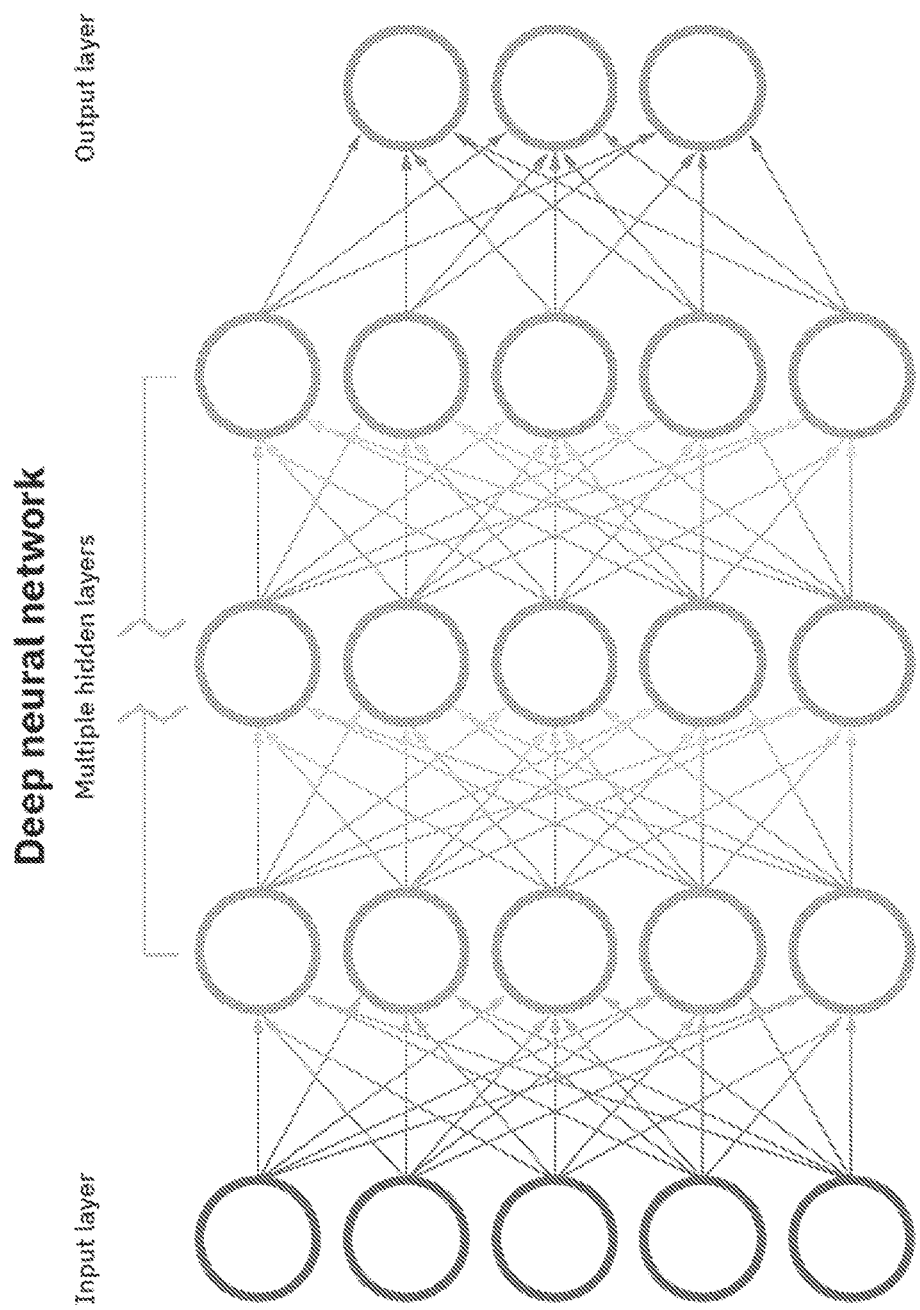
FIG. 3 shows an exemplary deep neural network.

FIG. 3 shows an exemplary deep neural network.

Neural networks, also known as artificial neural networks (ANNs) or simulated neural networks (SNNs), are a subset of machine learning and are at the heart of deep learning algorithms. Their name and structure are inspired by the human brain, mimicking the way that biological neurons signal to one another. Artificial neural networks (ANNs) are comprised of node layers, containing an input layer, one or more hidden layers, and an output layer. Each node, or artificial neuron, connects to another and has an associated weight and threshold. If the output of any individual node is above the specified threshold value, that node is activated, sending data to the next layer of the network. Otherwise, no data is passed along to the next layer of the network.

Neural networks rely on training data to learn and improve their accuracy over time. However, once these learning algorithms are fine-tuned for accuracy, they are powerful tools in computer science and artificial intelligence, allowing one to classify and cluster data at a high velocity. Tasks in speech recognition or image recognition can take minutes versus hours when compared to the manual identification by human experts. One of the most well-known neural networks is Google's search algorithm.

In some exemplary embodiments, one should view each individual node as its own linear regression model, composed of input data, weights, a bias (or threshold), and an output. Once an input layer is determined, weights are assigned. These weights help determine the importance of any given variable, with larger ones contributing more significantly to the output compared to other inputs. All inputs are then multiplied by their respective weights and then summed. Afterward, the output is passed through an activation function, which determines the output. If that output exceeds a given threshold, it "fires" (or activates) the node, passing data to the next layer in the network. This results in the output of one node becoming the input of the next node. This process of passing data from one layer to the next layer defines this neural network as a feedforward network. Larger weights signify that particular variables are of greater importance to the decision or outcome.

Most deep neural networks are feedforward, meaning they flow in one direction only, from input to output. However, one can also train a model through backpropagation; that is, move in the opposite direction from output to input. Backpropagation allows one to calculate and attribute the error associated with each neuron, allowing one to adjust and fit the parameters of the model(s) appropriately.

In machine learning, backpropagation is an algorithm for training feedforward neural networks. Generalizations of backpropagation exist for other artificial neural networks (ANNs), and for functions generally. These classes of algorithms are all referred to generically as "backpropagation". In fitting a neural network, backpropagation computes the gradient of the loss function with respect to the weights of the network for a single input—output example, and does so efficiently, unlike a naive direct computation of the gradient with respect to each weight individually. This efficiency makes it feasible to use gradient methods for training multilayer networks, updating weights to minimize loss; gradient descent, or variants such as stochastic gradient descent, are commonly used. The backpropagation algorithm works by computing the gradient of the loss function with respect to each weight by the chain rule, computing the gradient one layer at a time, iterating backward from the last layer to avoid redundant calculations of intermediate terms in the chain rule; this is an example of dynamic programming. The term backpropagation strictly refers only to the algorithm for computing the gradient, not how the gradient is used; however, the term is often used loosely to refer to the entire learning algorithm, including how the gradient is used, such as by stochastic gradient descent. Backpropagation generalizes the gradient computation in the delta rule, which is the single-layer version of backpropagation, and is in turn generalized by automatic differentiation, where backpropagation is a special case of reverse accumulation (or "reverse mode").

With respect to FIG. 3, according to exemplary embodiments, the system produces an output, which in turn produces an outcome, which in turn produces an input. In some embodiments, the output may become the input.

Figure 4:
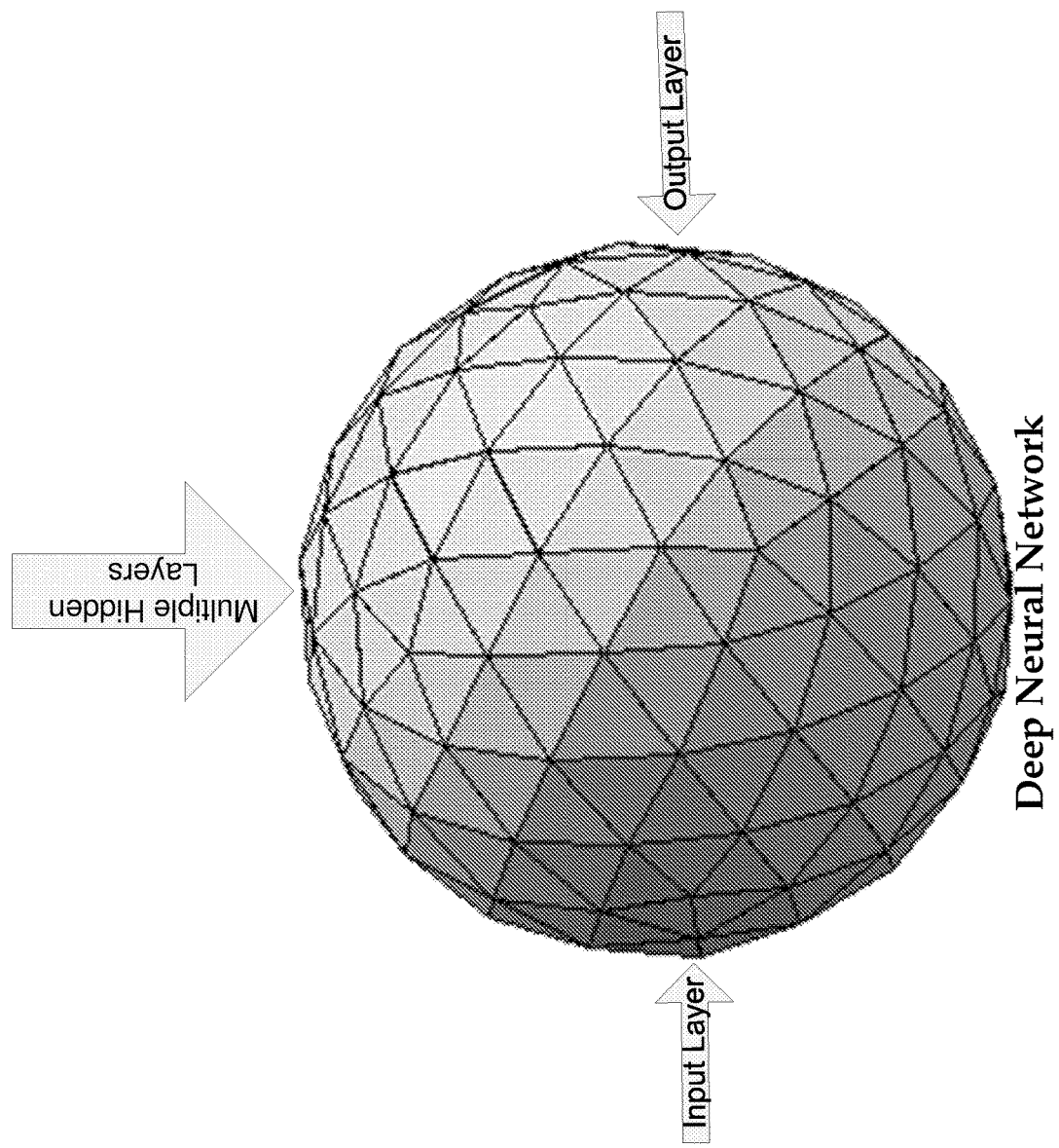
FIG. 4 shows another exemplary deep neural network in the form of a geodesic dome.
Figure 5:
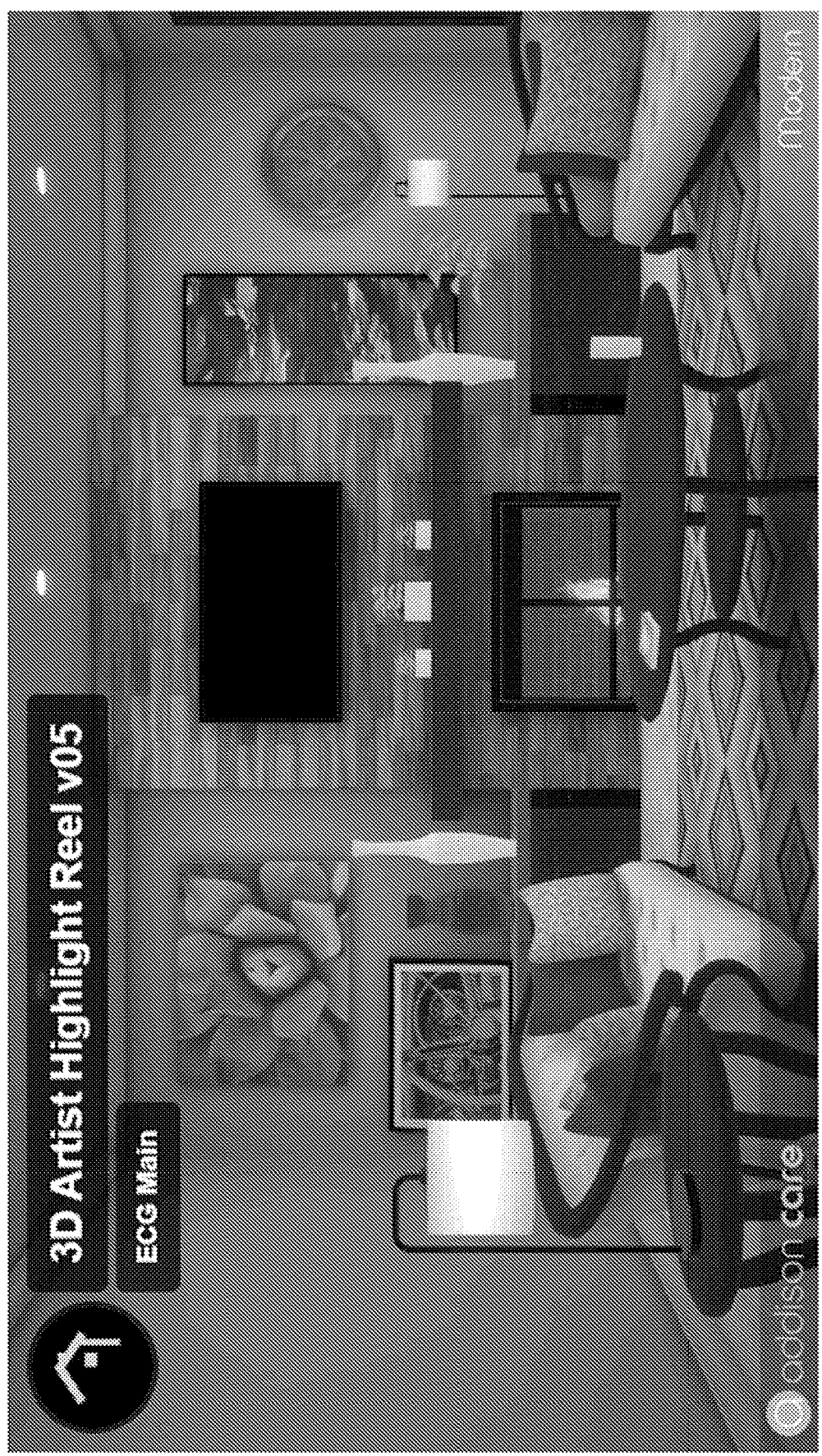
FIGS. 5-12 shows exemplary interior environments.
Figure 6:
Figure 7:
Figure 8:
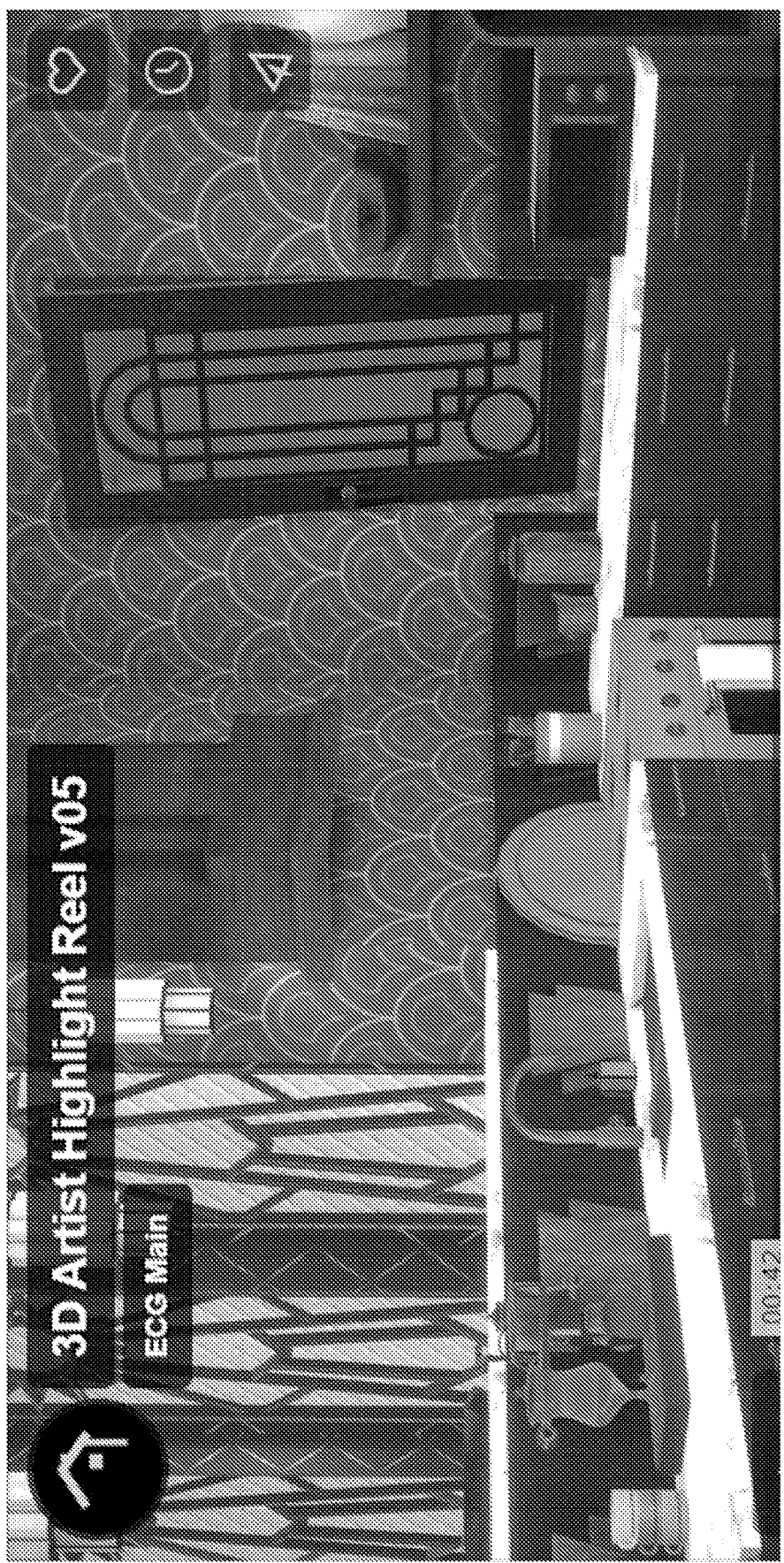
Figure 9:
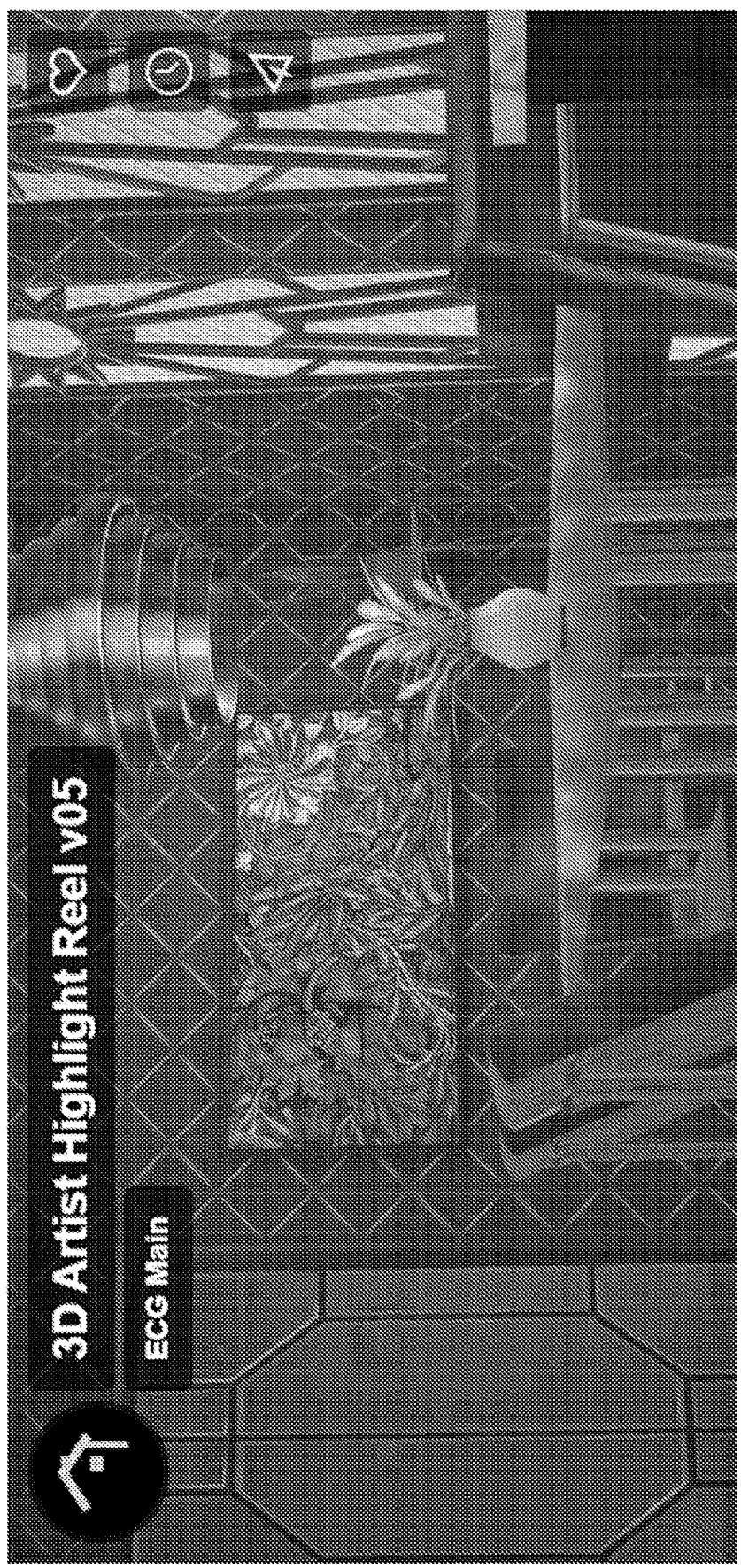
Figure 10:
Figure 11:
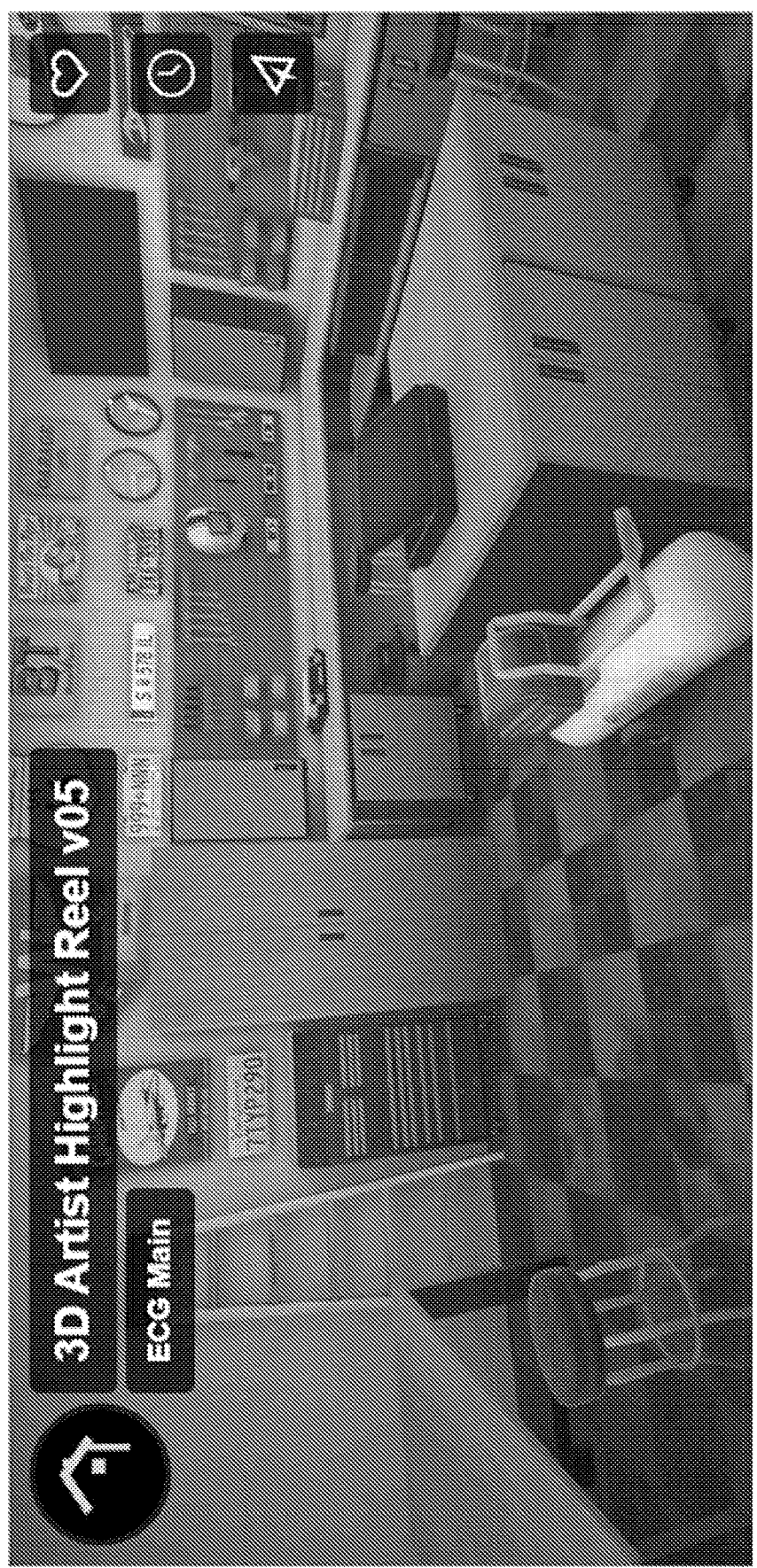
Figure 12:

FIG. 4 shows another exemplary deep neural network in the form of a geodesic dome.

Illustrated is a dynamic multi-faceted/multi-dimensional system, having an input layer, multiple hidden layers, and an output layer. With respect to FIG. 4, according to exemplary embodiments, the system produces an output, which in turn produces an outcome, which in turn produces an input. In some embodiments, the output may become the input.

Addison Description and Purpose.

Dynamic personalized technology-to-human interactive engagement interface to increase compatibility, utilization and to induce sustained behavioral change for treatment adherence and self-care.

Multi-faceted health assessment apparatus and combined software for integrated, precision remote patient monitoring including interactive behavioral health assessments, physical therapy assessments, care plan demonstrations, health monitoring device demonstrations, caregiver education and support, sentiment analysis, visual analytics for medication monitoring and management, health history information; early identification of health decline, adverse drug reactions, dosage analytics, therapeutic response to treatment plans and disbursement of health data and alerts to members of the care circle, including EHR integration, caregiver interfaces and applications and provider patient management platforms.

Dynamic hardware and software interface utilizing 3D animation, ambient mixed reality, Bluetooth, radio frequency, cellular communication, internet protocol, cloud computing, edge computing, 3D visual sensor, far field microphones, audio sound system, noise cancellation software, interactive touch screen, conversational speech technologies, procedural speech, facial recognition, API integration to external services, health network integration, machine learning, sentiment analysis of biomechanical and voice and facial analysis, connectivity to physiological biometric devices, 24/7 emergency response, health wearables and implanted health monitoring devices.

Monitoring, assessment and reporting of health decline, health stability, health improvement and indications of infectious disease.

Gait, balance and physical therapy demonstration and monitoring of compliance, rates of recovery and indications of non-adherence.

Optimized care coordination and measurement of treatment efficacy.

Predictive analytics enhanced by continuous, multi-faceted engagement, surveys, remote examinations and real time data observed through a modality of methods during the interrupted activities of daily living.

Improved treatment adherence where non-adherence is a primary cause of treatment failure.

Expedited, more informed intervention to preempt loss of life, adverse reactions to treatment, pain, suffering, treatment failures, and health complications.

Increased patient engagement and support to sustain behavioral change, increase ongoing encouragement, identify best practices, introduce reward systems for care compliance.

Early identification and coordinated communication of health decline and early identification of infectious for the purpose of faster, informed intervention and suppression of the spread of infectious diseases.

Atmospheric mirroring and experiential, personal association programs compel the user to form deeper and trusted bonds with the Addison technology interface, including 3D scenes which geo-target and mirror the patient-user's weather imagery and sound, time of day affecting lighting, shadows, sunrise, sunset, night time, day time; and preferred gender, ethnicities, language, décor, apparel, holidays, religion, color, preferred nickname, pets and product placement, landscape, hobbies, music, and preferred services such as ride share, grocery delivery, medical equipment and social connectivity with family and other patients with similar illnesses.

To evaluate multi-treatment directives which may reveal conflicts of care.

To fill the gaps of caregiving and provide affordable, seamless patient support, security, elder care education for users and supporting caregivers.

Engineered sentiment to further connect technology with user, including Addison 3D character gestures, expressions, tone of voice and mannerisms to apply sentiment and emotion such as concern, empathy, humor, sternness, compassion, love, joy, and confidence.

Idle mode entertainment features whereby the Addison 3D virtual assistant and caregiver projects an illusion of life and personal interests. During periods of non-engagement with the user Addison will appear to read, dance, clean, actively engage in hobbies, fitness, decorating, interacting with animals, engage in personal hygiene, modify scenes, listen to music, and other fluid and continuously alternating and frequently updated routines which can be tailored for user interests and preferences.

Enhanced gamification to excite users for health, wellness and fitness accomplishments, and to provide cognitive stimulation and memory support.

An enterprise level platform capable of managing individual health plans, health reminders, health surveys and assessments, deployed care routines for physical and mental health, individual device features ranging from images, personal, gamification and interactive routines, sound levels and operational metrics, remote technical support and integration between individual Addison systems and monitoring facilities, caregiver applications, providers, EHRs, EMRs, external services, and integration through API with available smart home connected devices ranging, but not limited to appliances, robotic and mechanical aides, cloud assistant features, security systems, audio/visual equipment, locks, 24/7 emergency response, care coordination operations for chronic care management and on-demand remote patient triage, connection to customer support, audio/visual telehealth platforms, and two-way calls to designated third parties.

Health history routines and features whereby the user can use voice or touch capabilities to review prior health measurements such as vitals, or to verify if a medication was taken and when.

Relational marketing and education. The Addison virtual assistant and caregiver can suggest health routines, education or make subtle suggestions for products or services introduced through the course of personalized engagements and available by touch or voice through the platform for purchase, or delivery.

Addison is designed to develop an unprecedented experience with the user. Addison deploys techniques originated from decades of neuroscience and applied to various industries ranging from news media to film, to social media. Many health devices, online websites, applications, chatbots and decision trees are underutilized and difficult to navigate and retain user attention when the patient using is experiencing cognitive decline, chronic pain, is medicated, has declining hearing or vision, declining sensitivity, nerve damage or distractions from chronic conditions.

Voice technology has developed a slightly improved ease of use but lacks the ability to develop a deep emotional or psychological attachment. Few users adopt and engage, fewer users continue with pre-Addison technologies.

Addison is designed to create a unique shared experience with the user. Addison presents an illusion of life and establishes intelligence quickly. She knows the user's care plan details, members of the care circle, and when engaging a user for the very first time Addison obtains personal information which is incorporated into the Addison scenes, engagements, conversations, and experiences.

In the film industry a viewer can experience a broad range of emotions and thoughts. The viewer knows the characters are not real, they are actors. Viewers know the film is built from scripted scenes and themes, laden with special effects and various locations. Yet the viewer will binge-watch a favorite show, experience emotions and respond to ideas and themed presentations as though they're real. Viewers experience varying levels of neurotransmitter stimulation and levels of oxytocin, serotonin and dopamine during viewing periods. Viewers become riveted to programming, on the edge of their seat one moment, anxious the next, relaxed a moment later, in the middle of the show they may be aroused, angry, or frightened. Viewers will sob in sweet sentiment, or sob in anguish while watching a production they know is fake.

Addison brings this method of stimulation to health care for positive outcomes and to compel patients and at-risk individuals in need of chronic care management, behavioral health support and health prevention, to buy-in to their own care, to adhere to treatment, and to safely communicate and disclose information otherwise suppressed out of fear of judgment.

By presenting a disarming 3D character, lifelike but not intimidating, the user is sweetly entertained by a character they know isn't real but captivated and impressed by the level of wisdom the Addison technology presents. Scenes are designed to deepen personal association in areas of likeness, culture, celebration, environment, and routines. Addison shares the user's preferences and experiences. Addison is meant to create a trusted and emotional attachment and is available 24/7 to support a user who may be struggling with a range of issues from chronic pain to addiction to depression or illness. Addison's support and care plan direction is seamless, easy, and dynamic. Addison becomes a companion and a hub of connection point between all members of the care circle, and those authorized, concerned and participating in care support and treatment.

Addison is specifically designed with captions, voice, dynamic user interface, living routines, clever anecdotes and convincing routines displaying intelligence, empathy, and concern to reinforce care regimens and faster identify health anomalies, injuries, security concerns, abuse of the user, and detailed analytics on treatment routines and responses. Addison services those with hearing and visual impairments.

Addison is engineered to instigate hormonal and neurotransmitter responses to elevate mood, conviction, dedication, confidence, and commitment toward personal care. Addison's layered 3D interactive environment, picture in picture, personalize experiential engagement features, and atmospheric mirroring delivers a human technology experience that takes voice interaction to a new level. Voice not only receives a face, body and personality, the Addison character produces an entire 3D animated environment involving dynamic exterior themes and landscapes, shared personal experiences and preferences, changing rooms, décor, color, conversations, interactive objects, and fresh evolving routines to support the illusion of life of companionship.

Addison is continuously updated so routines and updates create an experience that is fulfilling and engaging for the user. Addison's high level health compliance protocols, localized edge computing, facial recognition feature, and end to end data encryption protects personal health information and keeps communications between authorized users and the system.

Our systems and solutions never sleep, never run an errand, never take a day off and never forget. There is no more of an affordable and reliable way to place eyes on the patient than ECG digital care solutions. We extend care from behind the doctor's four walls and seamlessly direct it into the patient's home, delivering 24/7 reliable support.

Symptoms ebb and flow, they emerge and retreat. The patient often becomes numb to and used to their conditions. They fail to effectively describe or even remember the details of their conditions. Some details of their condition cannot be observed through human sight and hearing.

Much of what is going on with the patient is not present in a patient's health chart. There are conditions and coconditions that exist or emerge that can be difficult to interpret within a consultation. The doctor does not have access to actionable or real time data in order to more effectively comprehend patient conditions, routines, adherence, or to measure the effectiveness of applied treatment directives, or medications.

What we have invented is 24/7 passive, continuous monitoring of the patient through the application of more data collection methods than previously deployed or attempted in the home or extended care facility. With developing artificial intelligence applied to the data we are extracting from the patient's environment; we can make continuous evaluations and disburse actional data to providers and caregivers. Addison can observe granular details both visually viewed and heard through technology that human sensing cannot detect and is often not present to detect.

Addison coordinates the extraction of biometric physiological data, biomechanical data, facial recognition, survey driven patient feedback, medication management, activity patterns, variability, anomalies, embedded health history, pharmacology information, data about response to treatment, sleep and wake patterns, speed of patient response and decision, postural and facial evaluation, behavioral health inputs, adherence behavior, and additional sentiment analysis. Addison taps into vast digital health and research libraries and can leverage provider data for improved patient care and insights.

Addison can obtain, process, organize, index and present information to the health file for review by a doctor they have never experienced before. We can inform of critical insights in real time without delay. We can empower a doctor to make faster more accurate, more referenced decisions for treatment and diagnosis than has ever existed in history. By adding genomic data and advanced insights into how a patient is or will respond to medication for precision, personalized medical treatment, care can be enhanced and evaluated even further.

40% of America has a chronic illness which is 133,000,000 Americans. 80% have more than one chronic illness. 26% of our children live with a disability or chronic illness. Corporate America suffers up to $33.6 billion per year in lost production from full time workers doubling as caregivers. Live caregiving is affordable on a part time basis to only 3% of Americans due to high cost. Nearly 50 M Americans double as caregivers and they forget, sleep, run errands, bathe, take phone calls, and have little support to help them keep patients on track. Caregiver rates of personal illness are increasing from the stress related conditions of caregiving. Aging and ill individuals are less agile, vulnerable, and increasingly being victimized by intruders, scam artists, robberies, assaults and burglaries. 1 in 3 fall each year. Falls are a byproduct of hip, knee, ankle, foot, neurological, inner ear, neuropathy, footwear, slippery surfaces, spine, clutter and numerous other causes. Falls are the #1 cause of accidental death, traumatic brain injury and loss of functional independence. The average length of time to response after a fall is 18 hours.

Addison is an interactive, comprehensive health monitoring and assessment system. Addison is designed to provide continuous passive and active patient engagement and supervision, with care coordination and clinical workflows to provide improved outcomes, health prediction, care coordination, increased treatment adherence, to facilitate prevention, enable early identification of health status, improvement or decline, and to expedited more informed intervention.

One of the primary functions of the Addison 3D virtual caregiver is to create personalization and both a psychological and emotional connection with the User. The Addison display screen, voice and developing Addison personality and choice of words, establishes, maintains and increases the Addison Experiential Engagement Features (AEEF). There are 5 primary features to create AEEF and a technology engagement experience that is unprecedented:

UX Features Mandate

Atmospheric mirroring. Addison experiences and presents seasonal changes, weather changes, lighting changes, with visual and audible presentations that mirror the User's environmental experience. Interior and exterior effects complement atmospheric mirroring, such as Addison's fireplace functions automatically during colder temperatures.

Personalized engagement. Addison calls people by their name or preferred nickname, expresses and presents details about their preferences such as color, decor, gender, language, ethnicity, personalized care plan directives and monitoring, personal interests, third party services such as ride service, health services, advocacy services, insurance services, grocery ordering or delivery, customer service, care triage center, emergency response, and voice or touch driven text, two-way call, or social media posting to personal contacts. This creates a sense of companionship and connectivity for care and social satisfaction.

Emotional intelligence presentation. Through humanistic mannerisms, articulated body postures, speech cadence and pauses, body movements and gesticulations, humorous anecdotes, facial expressions, and tone of voice to express presentations of engineered empathy, concern, compassion, astonishment, surprise, curiosity, playfulness, wonder, aw, celebration, applause, sternness, apology, and the full range of human sentiment.

Dynamic variation. The Addison system receives continual deployments of updates to Addison interior and exterior scenes, updates to phrases, new synonyms, clothing, hair style, props, color, décor, furnishing, hobbies, amenities, product placements, mannerisms, physical and cognitive skills, and personalization for holiday themes, religious themes, are part of the invention for user satisfaction and peak engagement while captivating User's attention and curiosity.

Safe, enchanting form factor with illusion of intelligent life. Addison is designed to conjure a child-like enthusiasm ranging from both older adults to a child patient. Addison presents a somewhat mystical persona because though the 3D Virtual Caregiver is quite obviously a non-living animated persona, when the system speaks, moves, demonstrates, educates, manage health routines, delivers tutorials for helpful routines such as cooking, cleaning, dietary preparation, self-care, fitness, weight loss, and life-skills, Addison addresses Users by name and performs according to the User's personal preferences or needs. Coupled with atmospheric mirroring the User perceives intelligence and that is where the tantalizing and disarming charm and enchantment originates from.

General Feature Extrapolations.

When Addison speaks or is spoken to, she will present buttons with appropriate options for function or User responses and commands, such as a list of available features, or YES and NO, or cancel, or go back, or home, or privacy mode, or the telehealth service, or emergency response, or take vitals, or medications, or motion. At all times when Addison speaks her speech in real time will be displayed in text characters in a captioned box at the button of her screen.

In many cases where Addison seeks to direct a User to place their focus on a specific area of the screen the area may be highlighted or captioned, and other areas may be displayed as dim or darker.

Addison's display screen provides convenient information such as weather and time and the display and Addison onscreen environments operate in accordance with ATMOSPHERIC MIRRORING FEATURES (AMF). AMF means that Addison's 3D scene will mirror the User's environmental experience. The first AMF feature is seasonal and real time lighting and weather matching. Addison is connected to a weather service or devices which provide information on exterior weather conditions. Time monitoring adjusted for seasonal variations aide's adjustment to interior and exterior scene lighting effects. For example, Addison's scenes will mirror the User's exterior conditions. If it is dusk at the User's location the scene depicted outside Addison's windows in her projected Addison home will display an image of dusk. If it is midday and sunny, Addison's window view will be bright and sunny. If it is dark and raining at the User location it will be dark and raining outside Addison's windows and skylights. If the exterior weather at the User location is dawn, Addison's exterior home view is dawn. As seasons change from spring to summer to fall to winter, Addison's exterior view from her 3D home will mirror seasons. Cloudy days will result in clouds outside Addison's windows. During fall the trees outside Addison's windows change colors. During winter her trees have no leaves, unless they are evergreens associated with landscape choices or geographical considerations. During spring Addison's trees are budding and in Summer Addison's trees are green. If the wind is blowing leaves or debris will blow outside Addison's windows.

In the evening hours around dusk as the exterior of the user's environment grows dark Addison's windows will not only be dark or mirror lunar cycles and images, but the lights inside Addison's 3D home will also come on and her rooms will show lit lamps and natural glows from her interior lighting. They will remain that way throughout the night.

Addison dynamic variation shows Addison in various rooms for various routines and scenes. They are programmed on random intervals. Addison mirroring can be programmed to present the 3D character in a room selection to the room selection the User is in. For instance, if the User is in the kitchen or bedroom, Addison will be in her kitchen or bedroom. Addison libraries randomly rotate through selections or can be defined by the User. Examples of scenes include kitchen, pool area, jacuzzi, a living room, fitness room, rehab studio, front porch, front yard, rear yard, rear porch, bedrooms, bathroom and remote scenes such as beach scenes and mountain scenes. Dynamic variation keeps the User experience fresh and exciting, and is mesmerizing for all viewers in the vicinity, which increases the conversation and attention toward the system.

Primary Functions
   Addison Experiential Engagement Features (AEEF).
   Empathy, psychological and emotional engagement.
Atmospheric Mirroring Experience.
   Addison At Idle Transitions.
   Medication Reminders and response monitoring.
   Medication consumption monitoring.
   Medication consumption alerts.
   Adverse drug reaction monitoring (ADRs).
Sentiment Analysis.
   Vitals Reminders and acknowledgement monitoring.
   Vitals Readings monitoring.
   Vitals Device Demonstration.
   Vitals compliance and threshold alerts.
   General reminders and acknowledgement monitoring.
   Dual-window activity/inactivity monitoring.
   24/7 emergency response.
   24/7 physician on demand (the telehealth service) telehealth service.
   Physical therapy reminders and response monitoring.
   Physical therapy routine demonstrations.
   Physical therapy performance monitoring.
   Programmable Mental Health surveys with rating scale.
   General Physical Health surveys with rating scale.
   Gamification and rewards alerts.
Atmospheric Mirroring.
   Memory support and monitoring feature.
   Alexa/Google Home Integration for Q&A, timers and entertainment.
   Partial resource mode for redundancy and safety during loss of internet or power
Addison Product Overview
   Medication reminders and acknowledgement.
   Vitals reminders, readings, alerts and acknowledgment.
   Emergency response via voice, touch, peripheral console or wearable pendant device.
   General activity detection (any engagement or movement during 2-programmable windows of time.
   Basic rehab demonstrations.
   Third party virtual assistant connectivity such as Google home or Alexa.
   Voice or touch connect to customer service.
   Hand to mouth gesture monitoring during medication intake (optional on/off).
   Addison Pause—the ability to halt "First Addison Experience" routine to stall for User explanation.
   Addison STOP—the ability to stop Addison and return to home screen.
   Addison REPEAT—the ability to command Addison to repeat last question and subsequent response options.
   Addison RESUME or CONTINUE—the ability after pausing Addison to continue routine where she left off.
Partial Resource Mode.
   One of the superior benefits of Addison is reliability. Partial resource mode is an event where internet and/or power is lost. All critical functions and alerts continue to work leveraging the smart hub and connected devices over cellular with battery backup. The PRM features are described herein.
User Service Enhancements.
   Home Control—lighting, security, appliances (i.e.—Nest API controlled by Addison voice or touch commands) Ride Share—scheduling an Uber or Lyft ride via Addison touch or voice via API. Grocery Service—Grocery request, list and order via Addison touch or voice API. Addison Platform Order, User and Deployed Device Control.
Fleet Management.
   The Addison platform providers the ability to update and manage the fleet of devices for features, function, and monitoring in a seamless over the air update, providing real time deployment of customized directives, demonstrations, reminders and monitoring response and data associated with personalized care plans and routines for self-care and life management.
Order Architecture
   Activation and features parameters.
   Care plan directives.
   Billing details or third-party billing.
   Monitoring information.

Sales.
 Customer service account access, logging and disposition reports.
General Connectivity.
 IP.
 Associated Back up Smart Health Hub connected via cellular or IP.
 RF for long range devices including emergency response request.
  Wearable Pendant for emergency response.
  Automatic wireless Bluetooth or RF fall detector.
  Cellular Wireless connection for redundancy or primary function.
  Bluetooth Peripherals for vitals monitoring.
  API for 3$^{rd}$ party device and services connectivity.
Access Control Features (ACM).
 System platform provides dynamic, secure permissions and access control management levels for order entry and access to alerts and individual and group systems information, and both unprotected and protected user or User information data.
 If a health care organization or other care or administrative provider with an organizational network wishes to appoint full or partial access to account information, sales/activation/deactivation information, account activity, alert review or to receive active alerts or notifications from an individual office or a group of office users, the system facilitates it including:
 Protected Health Information with HIPPA authorization verification.
 Individual office only such as in the case of a local franchise or satellite office operation.
  General sales and cancellation activity only.
  Customer service event logs.
  Shipping information.
  Activation status information.
  Alerts and reminders.
  Health surveys.
 The virtual caregiver whether used as caregiver or virtual assistant, uses various options for security of User private or protected information including facial recognition, voice recognition, or access code or password.
Main tested hardware features.
  Power-up sequence and on/off feature.
  Display screen power, touch features and display.
  Annunciator lights.
  WIFI connectivity.
  Bluetooth connectivity.
  Camera function both 2D and 3D depth of field.
  CPU/GPU function.
  Audio Speakers.
  Microphones.
  Peripheral device connectivity.
  Edge compute.
  RF devices.
  Transmission reporting to third party services.
  Noise cancellation software.
Central Station Signal Management.
 Addison systems may be connected to 24/7 emergency response monitoring or care triage center. Transmissions may occur over integrated Addison display unit over IP, Bluetooth or cellular, or through an internal or external smart health hub providing additional backup power and wireless connectivity and transmission capabilities over cellular network in the case the main Addison display unit or console fails or loses power or internet.
 Central Station General Reporting and Alerts.
Addison Stand Alone Smart Health Hub
  Supervisory signals:
  Loss of AC power.
  Back up console or display unit battery low.
  Powering off.
  No pendant check-in.
  Programmable self-diagnostic test and report (we call it timer because it's a scheduled interval).
  Alarm signals and alerts.
  High priority pendant alarm.
  High priority base unit alarm.
  No response to med reminder.
  No response to vitals reminder.
  No response to general reminder.
  No response to hydration reminder.
  No activity detected.
  Improper or proper response to health survey engagement.
  Adverse drug reaction identified.
  Gait and balance monitoring.
  Variation to sleep or wake patterns.
  Variation to variation in activity levels.
  Status, rate of recovery, range of motion variation to physical motion analytics assessment.
  Auto fall alert.
  Incontinence sensor alert.
  Vitals monitoring threshold alert.
  Sentiment or mental health alert.
  Addison Supervisory signals.
  No IP connection.
  Cellular signal weak.
  Low pendant battery.
Addison Console Self Diagnostics Upon Power Up.
 System runs an automated self-check process upon first power up where custom visual indicators and sounds confirm status of internet, power, display, audio and mic test.
  IP connectivity.
  Power.
  Display Test.
  Audio Test.
  Mic Test
 FIGS. 13A-13F show examples of order entry specifications.
Diagnostic Test On Premises
  Power-up.
  Screen power and display/physically inspect and press to confirm.
  Annunciator lights/physically inspect and press to confirm.
  WIFI connectivity/on screen press to confirm.
  Camera function/sequence demonstration press to confirm.
  CPU function/displayed press to confirm.
  Speaker's test/interactive/press to confirm.
  Microphones test/talk to test and press to confirm.
  Check clock and atmospheric mirroring and press to confirm.
User Initialization Experience Overview
  User First and Continuous Experience.
  First time User interactive User tutorial and verification of primary information, name and reminders is the first User experience that occurs post installation and during the powerup and start sequence. The routine is designed to help the User understand all key Addison functions, her timing and cadence, and how to get "unstuck" if things do not go as anticipated.

Addison is always active. At rest and in-between scenes Addison always appears to be breathing for illusion of life. She will display a series of natural idle scene movements and pre-programmed routines which are continually being updated so scenes appear fresh in the market with continual updates to entire fleet, so scenes are dynamic, and so the User is entertained, curious and anxious to see what Addison will do next. Addison's simulated breathing and gestures provide continued illusion of life. To engage Addison responses and functions user will always either press or talk using wake word to signal an action from Addison.

Addison First User Experience (FAE) Example.

FAE begins with Addison initialization greeting. "Hi there, I'm Addison, welcome to Addison Care. It's so nice to see you. I'm so excited about being able to asset you with life and health care each day. Before I show you everything I can do, I'm going to share the basics of working with me. First, you will always see me here on the left side of the screen. At the bottom of the screen, you can always see where the time and weather are displayed. If you look at the bottom of the screen you will see some captions. Everything I saw will be shown down here. Interacting with me is simple when using my favorite button, the Addison button. You'll be able to use this button to get my attention and see what I can do at any given time. On the top right of the screen, you'll see a privacy mode (button. You can press this button at any time if you would like me to stop listening and give you privacy.

Go ahead and press the privacy mode button now." User pushes privacy button which turns red. Addison continues—"At this point I can't hear or see anything. So, I'll just be reading a book or listening to my music. To allow me to resume listening to you and using my visual sensor, touch the privacy mode button again." User presses red button and privacy mode is deactivated and turns back blue.

"Maybe you've noticed I have this fancy caregiver clipboard (Addison motions to her clipboard in scene, a shader box appears around it, the background blurs and Addison taps on the keys). When you say or press the Addison button my clipboard will turn green to show that I'm listening for a response or waiting for you to touch something on the screen at the top left of the screen we have the ASSIST button. You can tap this button or say Addison, ASSIST, if you ever need support. Go ahead and say or touch the assist button now. From her you can choose which type of help you would like.

This includes, emergency calls, User support questions, and access to the telehealth service. If you're ever having an emergency say ADDISON, HELP. As soon as I hear that I'll connect you with emergency services right away. You can also say Addison—Emergency.

Always wait to see my tablet is green and I'm listening before giving me any command. If you have an emergency just wait 2 seconds after saying Addison, and then give the command.

Before we continue, I just need to double check that I'm speaking to the right person. Am I speaking to (example customer name used here) Betty Gutierrez?" The screen will display a YES and NO button and Addison's tablet will turn green indicating she's listening for a response. If User answers yes or presses YES button, Addison continues. If User answers no or presses the NO button Addison says—"Uh oh, let's get this corrected. I'm contacting User service now." Addison initiates an IP telephonic call to ECG User service and displays a call is in process presented on a digital plaque with a cancel button displayed. If onsite representative pushes the cancel button the call is terminated and Addison reappears and responds—"the call is cancelled, please let me know when you're ready to resume and we'll pick up where we left off".

The representative can then access the Addison care portal online and update the User information. If the call is continued and not cancelled an ECG User service agent will answer to open a duplex two-way telephonic call and the plaque will update to the message—CALL CONNECTED. The ECG operator will update the order information and disconnect, and the account information will be updated over the cloud. When the call is disconnected Addison will reappear and will present a button titled—RESUME. If the User or representative says Addison—RESUME presses the resume button the initialization routine will continue from its most previous segment and Addison will say—"I just need to double check I'm speaking to the right person". Am I speaking to Betty Gutierrez?" Addison's tablet will turn green to indicate listening for a response. If the User responds YES by either voice or using the YES button the initialization routine continues.

Note—typically if something is wrong Addison will tell the customer—"okay, once we're finished with this process, I'll contact customer service and we'll make any and all corrections" and then she continues. The name is a primary relationship development function, and we want to get it right at the beginning.

If the representative cancels the User service call Addison will reappear with a button that says RESUME. The representative can update the account information directly online which will update the profile via the cloud. If the User or representative presses the resume button the initialization routine will continue from its most previous segment and Addison will say—"I just need to double check I'm speaking to the right person". Am I speaking to Betty Gutierrez?" Addison's tablet will turn green to indicate listening for a response. If the User responds YES, the initialization routine continues.

Addison will ask—"Is your date of birth 1937 (as an DOB example)?" Addison will display a Yes and NO button and her tablet will turn green. If the User answers or says NO, Addison will respond with—"Okay, at the end of this process we'll connect to User service and make all required corrections. Let's continue". (The representative is expected and trained to keep a written list of any required changes through the initialization process.

This initialization process can also be supported through a remote telephone call if no representative is present, and an Addison Care system is self-installed or installed with a family member's support which is an option. If the User answers YES, then the initialization sequence continues.

After calling my name make sure to wait for the tablet to turn green before asking me a question, asking for help, or giving me a direction. Let's try the whole thing out, say Addison, and when the tablet turns green say—FAVORITE COLOR, and we'll start a conversation" User says ADDISON, tablet turns green, User says FAVORITE COLOR. The green light on Addison's tablet goes out and Addison responds by presenting a color pallet in her scene and says—"I love colors. What's your favorite color from the ones shown?" Addison tablet screen turns green, and she listens for response. User chooses color from color pallet. In this example User says—PURPLE. Addison hears the User response; her tablet light goes out and she repeats the User selection as follows—"I like purple too" and Addison's outfit transforms to purple. Addison continues. "At the top of the screen you'll see my favorite button, the Addison button."

FAE Care Plan Review

It is important for both customer trust, impressing the customer and account verification that certain FAE review items are included in the First Addison Experience. These items for review may and often include information such as:
Name
DOB
Display of Medications and Reminder Schedule
Display of Vitals Type and Reminder Schedule
Display of Health Survey Schedule for Assessment Questions
Display of any Rehab Reminders and Schedule
Preferred Hospital
Primary Care Physician's Name
List of Responsible Parties we notify Medication Support Overview.

If the User has required, elective or prescribed medications or supplements the system can be programmed via the activation or User portal for updates to deliver programmed reminders via voice instruction, visual display, acknowledgement and verification processes.

Each reminder will seek acknowledgment from the User to advance the reminder routine and to silence the medication reminder alert and to prevent non-adherence signals to be sent to the Addison Platform Database, Provider Portals and Care Team mobile apps. The embedded visual sensor will monitor hand to mouth gestures to verify a basic level of medication consumption indications.

Medication Reminders and response monitoring examples of a programmable routine.

The Addison platform allows unlimited medication reminders, scheduled daily or on any intervals, 7 days a week. If a scheduled reminder has been programmed into the Addison Platform for a particular User, upon the designated time to alert the User the Addison console will sound an alert, present a graphical alarm image on the display screen with animation effects with text that says Medication Reminder and a button that says—Alarm Off. The audible alert sound should be attention grabbing but not irritating and should reflect a frequency range which can be detected by an average 80-year-old patient with mild to moderate hearing loss. If the alert is acknowledged by the User by speaking the command "Addison . . . Alarm Off" or by pressing the button that indicates Alarm Off the display alarm graphic will stop animation effects and the audible alert will stop and the display screen will transition to Addison speaking while concurrently displaying her words in the real time speech text box at bottom of screen. Addison will say User's name to address them with a permission request such as "Ms. Caroline, I have a message for you, are you ready to hear it?" and Addison will display buttons that indicate YES or NO or NOT NOW, and her tablet will display green and Addison listens for a response. If the User presses NO the medication reminder will be snoozed (delayed) and Addison will announce—"okay, I understand you're not ready to take your medications now, I will remind you again in [default value] minutes. After [default or selected value] minutes has passed, the Addison system will repeat the alarm and will allow the default or selected value number of subsequent snooze cycles.

If the User does not respond to a medication reminder alert the alert will continue to audibly sound and display the customer reminder animation for the duration of the designated or default value selected at the time the system was ordered, or according to the last User account update that occurred if the original value was changed. If the designated number of repeat alerts does not receive a response from the User, the system will transmit a medication failure alert to the monitoring facility software and deposit the alert in the company database and update any designated $3^{rd}$ party provider and caregiver portal and transmit an alert to any or all designated responsible parties within the care circle on their ECG android or iOS device. If the User responds by voice or press of YES button to a medication reminder the alert will be silenced, the reminder animation graphic will stop and vacate the screen. The display will present scheduled medications to take, and Addison will announce, "okay, it's time for you to take [dosage information} i.e., 1 dose of lisinopril for blood pressure and 1 dose of Lipitor for cholesterol. Press done when you have completed taking your medications. The system offers multiple options of verification to step the user through taking medications one at a time, or all at once, and the system displays type of medication (pill, injection, topical, etc.). The medication name and instructions are displayed in fields in a graphical representation on the screen and remain static until the routine is finished. If the User has an injectable medication such as insulin during the account setup, the text entry field for medication type will allow the ECG rep to enter the speech instructions such as, "your recommended insulin dosage is 200 units), or the sequence of dosage information. A command should exist so that each dose is listed and separated by the text entry AND displays the next dose to the next drop-down dosage field on the display screen medication graphic automatically (i.e., one dose of lisinopril AND 1 dose of . . . ).

If after 5 minutes the user has not said "Addison done" or presses the done button Addison will inquire with the User by asking "Ms. Caroline, are you still there?" If the user does not answer Addison will repeat the question 2 more times, 5 min apart. If the User has not responded to the designated number of repeat inquiries the system will transmit a medication failure alert to the monitoring facility software and deposit the alert in the company database and update any designated $3^{rd}$ party provider and update the caregiver portal and transmit an alert to any or all designated responsible parties within the care circle on their ECG app on android or iOS device. If the User says "Addison done" or presses the done button Addison will acknowledge the response by saying "Great, your next medication reminder is at _:_ [designated value] and I will remind you when it's time (this routine will use random comparative phraseology to keep it interesting such as "wonderful, we're making great progress managing your health. Your next reminder is . . . etc., etc.).

Medication Consumption Feature.

Coinciding with the medication reminder is a monitoring consumption feature (MCF). If the medication consumption feature has been designated as active the MCF activates at the time of a medication reminder. The MCF will operate using an installed Depth of Field Camera. If the User acknowledges they are ready to take their medications in response to the medication reminder, the visual sensor will monitor indications of hand to mouth gestures consistent with medications being placed in the mouth and consumed or a glass being raised and indications of swallowing, which algorithms monitor to train the model over time.

During Medication routines Addison instructs the user to align themselves with the camera, using a visual picture in picture image to verify the User is properly positioned.

The system will log and provide alerts based on medication consumption, compliance or non-compliance programmable features. Authorized care circle members will be able to view the logs and a trend chart of yes or no indications and consumption monitoring indicators to monitor real time, current or historical data.

Memory Support & Monitoring.

Many Users will complete a health plan activity and moments later may forget if they followed through and complied. Addison is designed to assist with this common health challenge that leads to complications and poor outcomes resulting from non-adherence, by providing critical feedback to the User during moments of confusion and inquiry.

If Addison records vitals reading or provides a medication, hydration, nutrition, or mobility reminder she will make both the most recent activities and information available to the User upon request, as well as prior history. For example, in one of the programmable functions if the User says the wake word "Addison" (Addison's tablet turns green) followed by "I can't remember", Addison will respond by saying—"okay, that's what I'm here for Ms. Caroline. Just tell me what you can't remember. You can say, I can't remember if I took my medications, or I can't remember if I took my vitals, or I can't remember if I hydrated, or I can't remember if I did my mobility routine and I will check for you." Addison's display will present five buttons, one that says Vitals, Medication, Hydration, Nutrition or Mobility. Addison tablet will turn green If the User responds with "I can't remember if I took my vitals" or presses the vital button, or any corresponding button to the event requested to verification. Addison will say "Okay, let me check".

To overcome the sense of latency Addison will tap on her tablet as the data is extracted. If the User took their last vitals readings on schedule Addison will then present the most recent vitals activity both graphically and by saying—"I show you measured your blood pressure and your pulse and blood oxygen levels at 12 p.m." Addison will also announce the next upcoming vitals activity. "The next time to record vitals is tonight at 8 p.m. I'll remind you when it's time" Addison will randomly encourage the User with alternating phrases such as—"You're doing a great job following through on your care plan". Addison will then transition to her idle routines. Addison will make a similar announcement for any corresponding inquiry such as medication, hydration, nutrition or mobility.

If the User did not take their last scheduled vitals reading (or other activity) Addison will instead respond to the User's inquiry with an alternate outstanding vitals reading message—"Mr. Caroline, I show you were supposed to record your blood pressure and your weight at 12 noon and have not yet completed it. Are you ready to take these readings now?" Addison will display two buttons YES and NO, or LATER. If the User says YES or presses the YES button Addison will provide existing instructional comments to the user followed by "Press or say done when you're finished" and will present a button on her display that says DONE. If the User takes both readings Addison will wait for the User to press the done button.

As each reading is taken Addison will acknowledge verbally announce and present the reading on her display. If 5 minutes passes and the User has not taken a reading Addison will ask the User if they're still there, her tablet will turn green, and she will listen for a response and present a YES and NO button. If the User says YES Addison will ask the User if they need assistance. If the User says or presses YES Addison will say—"Okay, let me send a message to your care circle and get someone to call you". Addison will then transmit a message via text to the designated care circle priority contacts that says—"Mr. Caroline would like a call. She's having trouble taking her vitals." Addison's display screen will revert to displaying the Medication and Vitals button and she will behave in idle mode waiting for a verbal or touch input.

If the User responds to Addison's questions about needing assistance with NO, Addison will continue to wait an additional 5 minutes. If the User has not taken a reading after the second 5-minute period times out Addison will ask the User if they're ready to take their vitals and present a YES and NO button. If the User answers NO after consecutive attempts and cannot take a reading Addison closes the loop and says—"let's try again later, logs the uncompleted event. If the User took medications, Addison will explain, as an example, "I show you took 1 dose of lisinopril and 1 dose of Lipitor at 8:30 {most recent timer Addison will then present the next upcoming medication with a script that indicates she will remind the patient when it's time to comply.

Medication History.

The User may ask Addison using the wake word and prompt for medications to call up medication history. If medication history is activated and requested Addison will present a chart showing the prior 24 hours of medications presented and status of whether they were confirmed as taken (done) by the User and will verbally announce what's on the chart. Audible and visual review is important for Users that are hearing or visually impaired.

Medication consumption alerts training modules.

Addison uses training algorithms while monitoring general movements and indications at the time of medication consumption, logging and assessing dosage "count" indicators. This data can be flagged to watch for excessive dosage or when a User appears to not be dosing, or under dosing. This system will log data if a User responds with the DONE command and has not appeared, according to the depth of field camera or audio sensors, to have ingested medications. This count will lead to an alert whereby we can consult the care circle to have them inquire with the patient, check on their pill quantities and further investigate dosage habits, or provide a wellness check. Parameters for responsive actions are programmable.

The depth camera will assess more granular data such as subtle movements of the head consistent with verifying consumption behavior as well as monitoring the movements of the throat area to identify attempts to circumvent the system by feigning consumption, pretending to be swallowing or ingesting medications. If the User is identified as potentially attempting to deceive the system, the provider and caregiver platform can be notified and/or a notice transmitted to the Care Circle App.

The company also uses the 2D or depth of field camera to identify medication number and type held in the hand, and monitoring application routines such as topical applications, wound dressing changes and verification of compliance with injectable medications.

Adverse Drug Reaction Monitoring

Addison is designed to monitor for adverse drug reactions through multi-point data analysis. If the User has consumed medication and the depth of field camera identifies a measured deviation in postural stability such as excursions from center of mass as a sign of instability, or gait anomalies assessed through the gait and motion analytics (i.e. significant reduction in linear gait velocity, change in cadence, time in swing, time in double support, stride length, sudden sideward trunk lean, festination, retropulsion, etc.), Addison will flag the patient file to indicate an anomaly for AI training purposes and analysis, while engaging the patient to further survey and assess response to medication or treatment protocol.

If the User shows biomechanical decline on a defined scale of degradation (scale of 1 to 10 with 10 being most dramatic decline) after consuming medication Addison will engage the User to conduct a wellness survey. Addison will say—Mr. Caroline, I have a question for you, may I ask you now? Addison's tablet will display green showing she's listening, and her display will present a YES and NO button.

If the User responds NO, Addison will log the prior data and the User response inside the ECG provider and caregiver portal. Addison will answer to the NO response by saying—"Okay, remember, you can always say Addison HELP, if you have an emergency and I can connect you with our emergency care center and you can also ask me to contact the telehealth service if you'd like to speak with a doctor at any time, 24/7." Addison will then transition to her idle screen.

"If the User responds with YES by either voice response or pressing YES button Addison will make a statement followed by a brief number of inquiries. Addison will say—"I've noticed some changes in the way your body is moving. Are you experiencing any discomfort?" If the User response is either Yes or No by voice or touch screen Addison logs the response and continues through a sequence of defined inquiries "Are you feeling differently since taking your medication?" User responds yes or no. "Are you feeling dizzy?" User responds yes or no. "Are you feeling nauseous?" User responds yes or no. "Are you experiencing any changes to your hearing, or vision?" User responds yes or no. If the User answered YES to any question Addison will say—"You said you were [repeats condition or conditions] (such as—"you said you were feeling dizzy and experiencing discomfort"), would you like me to have someone contact you to talk about this condition?"

If the User says YES Addison will respond with—"I will let members of your care circle know and instruct them to call you. Remember, you can always say Addison, HELP, if you have an emergency and you can always ask me to contact the telehealth service if you'd like to speak with a doctor at any time, 24/7." Addison will update and flag the User file in the ECG provider and caregiver portal and transmit an interactive text message to Responsible Parties priority #1-#3 via the Care Circle Apps with a message that says—"Ms. Caroline is not feeling well and would like someone to call and check on her." (Not the "her" as designated by the gender selection from the order architecture).

If the User responds NO, Addison will log the engagement and responses inside the ECG provider and caregiver portal and transition to her idle screen display. If the User demonstrates indications of an Adverse Drug Reaction future Addison editions will evaluate changes in countenance via facial recognition to look for material changes which are show a decrease in positive disposition (has User's expressions and facial features transitioned to a frown, furrowed brow, droopy eyes, contorted strain, etc.) and has body posture decline to indicate negative anomaly such as slouching excessively, doubled over in pain, grabbing counters or chair backs for balance, etc. These future data evaluations will be used to train AI models for advanced assessments. Addison will monitor for indications based on updated inputs to the User profile indicating new medications or dosage instructions have been introduced to provide improved references to anomaly detection.

Slurred speech will also be searched for as well as significant changes to decision or response speed. During examinations Addison will couple monitoring for slurred speech with potential indications of conditions such as stroke where facial droop or the inability to move or properly control appendages on one side of the body or other. It is important we develop methods of initiating contact or response from responders or care circle when a User has become abruptly unintelligible.

Sentiment Analysis

During Addison engagement and using facial recognition to track and log overall consistency of base-line mood and expression such as smile/happy, neutral, frown, distress, sadness, or anger. The system will log indications of emotion which should be added in future updates to the User provider and caregiver portal. An overall percentage index of various emotions should be viewed according to a graphical scale based on the number of indications per day, per week, per month and per year. IE—the User presented a neutral expression 60% of the time, happy 30% of the time and showed sadness 10% of the time. Consistent emotional trending segments of time is reflected in color coded segmented lines to extended periods or changes in countenance and mood can be recognized quickly, which can aid a care provider to examine extenuating circumstances which may have caused the shift in countenance and mood. During Addison engagements the listening platform of the Addison console will assess voice patterns for significant anomalies which may indicate a health condition, change in mood or countenance and signs of discomfort. If the system hears indications of discomfort or distress such as gasps, shortness of breath, grunts, or slurred and elongated speech, or speech patterns inconsistent with typical daily engagements, Addison will complete the current engagement, whether vitals reading or medication routine, or mental health survey or emergency response engagement, or telehealth call or physical health or mental health survey, and then Addison will transition to conduct additional health surveys.

If the User shows irregular speech pattern based on indications, on a defined scale of indications and instances (scale of 1 to 5 with 5 being the greatest number of instances during an engagement) Addison will engage the User to conduct a wellness survey. Addison will say—Mr. Caroline, I have a question for you, may I ask you now? Addison's tablet will display green showing she's listening, and her display will present a YES and NO button.

If the User responds NO, Addison will log the prior data and the User response inside the ECG provider and caregiver portal. Addison will answer to the NO response by saying—"Okay, remember, you can always say Addison HELP, if you have an emergency and I can connect you with our emergency care center and you can also ask me to access telehealth provider if you'd like to speak with a doctor at any time, 24/7." Addison will then transition to her idle screen.

"If the User responds with YES by either voice response or pressing YES button Addison will make a statement followed by a brief number of inquiries. Addison will say—"I've noticed some indications you may not be feeling well today. Are you experiencing any discomfort?" If the User response is either Yes or No by voice or touch screen Addison logs the response and continues through a sequence of defined inquiries "Are you feeling pain?" User responds yes or no. "On a scale of one to 10 with 10 being most painful, what is your pain level?" Addison's tablet will be green to show she is listening for a response and her display will also display a graphic during this question as a reference for the User and a slider where the User can either slide the indicator to the corresponding number on the scale to reflect their level of pain or the User can answer with a number 1-10. Addison will log the response User responds yes or no. "Are you feeling nauseous?" User responds yes or no. "Are you experiencing any changes to your hearing, or vision?" User responds yes or no. If the User answered YES to any question Addison will say—"You said you were [repeats condition or conditions] (such as—"you said you were feeling dizzy and experiencing discomfort"), would you like me to have someone contact you to talk about these/this condition/s?"

If the User says YES Addison will respond with—"I will let members of your care circle know and instruct them to call you. Remember, you can always say Addison, HELP, if you have an emergency and you can always ask me to contact the telehealth service if you'd like to speak with a doctor at any time, 24/7." Addison will update and flag the User file in the ECG provider and caregiver portal and transmit an interactive text message to Responsible Parties priority #1-#3 via the Care Circle Apps with a message that says—"Ms. Caroline is not feeling well and would like someone to call and check on her." (Not the "her" as designated by the gender selection from the order architecture).

If the User responds NO, Addison will log the engagement and responses inside the ECG provider and caregiver portal and transition to her idle screen display.

Activity Monitoring.

Addison monitors a User's general movement or activity using either a 2D camera or depth of field camera. Multiple programmable activity periods, representing a duration of time between 1 and 36 hours can be programmed into the User profile using the platform or customer service interface. If start and end times for any period, the system may be instructed to monitor for activity are not given a value no activity monitoring will be active. Once an activity period or periods is established with a start and end time and if the User uses the Addison Wake Word, or responds to an Addison engagement, or touches any button on the Addison display screen, or uses the emergency response service, or walks within the viewing areas of any Addison console's depth of field camera an activity will be logged. If there is inactivity and no engagement with the User of any kind within the designated activity period an alert is updated in the central station software, the provider and caregiver portal and an inactivity message is transmitted to the Care Circle Apps which reads—"We have seen no activity for the past {designated number of hours)_hours from Ms. Caroline". If another person is present at the residing location of the Addison system and triggers an activity by movement or other system engagement the system will log an activity and no further action will be taken (it is assumed with a person present adequate supervision exists within the User environment). The central station software can be optionally programmed through its existing software to also provide an IVR notification to Responsible Parties upon inactivity alerts.

For future Addison editions we will seek to train our AI and analytical models to clock and monitor activity at a more granular level such as monitor length of sleep, length of inactivity, frequency of sleep, and frequency of activity to see how various behaviors and patterns during the activities of daily living coincide with physical and mental health conditions, acute episodes, recovery, and treatment plan formulations. This will include inputs from general gait and balance monitoring.

Stop Function.

At any time, the Addison wake word is used during a routine and the command STOP is given by the User Addison will halt her routine and respond with a pre-programmed gesture and Addison will respond with "Okay . . . I'll stop" and resort to her idle screen.

Vitals Reminders and Data Monitoring.

The Addison platform offers unlimited programmable vitals reminders, scheduled daily or on any interval 7 days a week, 365 days a year. If a scheduled reminder has been programmed into the Addison Platform for a particular User, upon the designated time to alert the User the Addison console will sound an alert, present a graphical alarm image on the display screen with animation effects with text that says Vitals Reminder and a button that says—Alarm Off. The audible alert uses a frequency range which can be detected by an average 80-year-old patient with mild to moderate hearing loss.

If the alert is acknowledged by the User by speaking the command "Addison . . . Alarm Off" or by pressing the button that indicates Alarm Off the display alarm graphic will stop animation effects and the audible alert will stop and the display screen will transition to Addison speaking while concurrently displaying her words in the real time speech text box at bottom of screen. Addison will say User's name to address them with a permission request such as "Ms. Caroline, I have a message for you, are you ready to hear it?" and Addison will display buttons that indicate YES or NO and her tablet will display green and Addison listens for a response. If the User presses NO the vitals reminder will be snoozed (delayed) and Addison will announce-"okay, I understand you're not ready to take your vitals now, I will remind you again in [default value] minutes. After [default or selected value] minutes has passed, the Addison system will repeat the alarm and will allow the default or selected value number of subsequent snooze cycles.

If the User does not respond to a vitals reminder alert the alert will continue to audibly sound and display the customer reminder animation for the duration of the designated or default value selected at the time the system was ordered, or according to the last User account update that occurred if the original value was changed. If the designated number of repeat alerts does not receive a response from the User, the system will transmit a vitals failure alert to the monitoring facility software and deposit the alert in the company database and update any designated $3^{rd}$ party provider and caregiver portal and transmit an alert to any or all designated responsible parties within the care circle on their ECG android or iOS device. If the User responds by voice or press of YES button to a vitals reminder the alert will be silenced, the reminder animation graphic will stop and vacate the screen. The display will present scheduled vitals to take, and Addison will announce, "okay, it's time for you to check your [vitals information} i.e. blood pressure and weight. If more than one vital is selected during the same designated time period Addison will display all vital routines in sequence. Addison will say please touch or say READY when you have your device and are ready to check (vital designation) your i.e.: blood pressure. You can also say tutorial if you need me to demonstrate how to use the device." If the User opts to for a tutorial once the tutorial is completed Addison will repeat—"please touch or say READY when you have your device and are ready to check (vital designation) your i.e.: blood pressure."

Once the vital is taken and the Addison device will store data and transmit to the cloud and will verbally and visually confirm the reading has been received. taken to the Addison scene. For example, Addison will report the reading-"your blood pressure is 180 over 120" with an additional acknowledgement that "your blood pressure reading is within threshold. This is great!" (Or rotating praise phraseology). If the blood pressure is out of threshold Addison's additional phrase after the reading report will say—"your blood pressure reading is out of threshold. I will let authorized members of your care circle know right away" and the scene will transition to the idle screen and a vitals alert will be transmitted to the care circle app and an alert and flag will be sent to the clinical portal and an IVR call will be made to a nurse's desk and/or a responsible party in the family care circle. Multiple notifications via the monitoring software for IVR exists through the platform.

If another vital alert exists at the same time Addison will continue with the message—"Now, it's time to check your i.e.: weight. If you're ready to check your weight, please step on the scale and say READY. If you need me to demonstrate how to use the scale you can say TUTORIAL. If the User says tutorial Addison will demonstrate using the device and will repeat—"please touch or say READY when you have your device and are ready to check (vital designation) your i.e.: weight." Once the vital is taken and the system receives it, Addison will report the user's reading, for example—"your weight is 135 lbs. and an additional acknowledgement that "your weight is within threshold. This is great!" (Or rotating praise phraseology). If the weight is out of threshold Addison's additional phrase after the reading report will say—"your weight reading is out of threshold. I will let authorized members of your care circle know right away" and the scene will transition to the idle screen and a vitals alert will be transmitted to the care circle app and an alert and flag will be sent to the clinical portal and an IVR call will be made to a nurse's desk and/or a responsible party in the family care circle. Multiple notifications via the monitoring software for IVR exist at the central station and in our new software to be installed at the time we activate our own monitoring center.

The system is programmable to display, track and announce rewards or warning notices to recognize progress or digression from the indicated goal and will correspond with an appropriate message of warning or encouragement to be coupled with rewards and gamification routines. Gamification includes point systems, ratings and badges, the ability to unlock new product features and services, or achieve status that can be converted for gifts.

Addison will continue this process until all vitals readings required during the scheduled period have been taken or rejected by the User, at such time as corresponding data updates will be logged or sent to care circle apps, monitoring software and/or clinical portal.

When the routine/s are completed, Addison will say "Press done when you have completed taking your Vitals. If after 5 minutes the user has not said "Addison done" or presses the done button Addison will inquire with the User by asking "Ms. Caroline, are you still there?" If the user does not answer Addison will repeat the question 2 more times, 5 min apart. If the User has not responded the designated number of repeat inquiries the system will transmit a non-response alert to the monitoring facility software and deposit the alert in the company database and update any designated $3^{rd}$ party provider and update the caregiver portal and transmit an alert to any or all designated responsible parties within the care circle on their ECG app on android or iOS device.

If the User says "Addison done" or presses the done button Addison will acknowledge the response by saying "Great, your next vitals reminder is at _:_ [designated value] and I will remind you when it's time (this routine will use random comparative phraseology to keep it interesting such as "wonderful, we're making great progress managing your health. Your next reminder is . . . etc., etc.).

Vitals History.

The User may ask Addison using the wake word and prompt for vitals to call up vitals' history. If vitals history is activated and requested Addison will present a chart showing the prior 24 hours of vitals presented and status of whether they were taken (done) and the reading received and will verbally announce what's on the chart.

Partial Resource Mode.

Addison offers multiple points of redundancy. When Addison loses internet connection and/or has inadequate power to function the voice and alerts (reminders, emergency response, etc.) a cellular back up connection and built in back up battery supports critical functions such as vitals monitoring and alerts, medication management routines, 24/7 emergency response and telehealth connection, known as critical routines. An additional voice based smart health hub may be provided as an option with a second set of redundant capabilities to handle critical routines.

Addison Idle Screen

Addison's idle screen is when she's idle between routines or not being engaged by a User. Addison idle screen displays time, date, weather and buttons for Privacy on/off, Addison Assist (which prompts a quick tutorial of available Addison features) and buttons for Medication routines, Vitals routines, Fall Risk Assessment and More Features. During idle presentations atmospheric mirroring (weather, day/night scenes, etc.) is active and Addison transitions through numerous idle routines such as breathing while still, scratching her nose, napping, engaging in a virtual hobby, listening to headphones to simulate music enjoyment, watching videos on her tablet, and lifestyle routines. These routines exist now, and additional routines will be continually updated so users are always interested and surprised to see new mannerisms, features or movements they haven't seen before. User interest and captivation is critical to Addison satisfaction, engagement and illusion of life.

Addison Assist Button (always at top left of Addison screen).

By touching the Addison Assist button or providing the command "Addison Assist" Addison will transition her screen to display various options with an existing voice narrative including:

Emergency calls summon emergency response by touch or saying Addison, Emergency or Help The telehealth service call to request physician or nurse care center consultation Customer service call to request technical support Tutorial to repeat First Addison Experience for user training Access to $3^{rd}$ party virtual assistant account features and skills Calls to designated, optional third parties such as external service, family or friend.

Emergency Response.

If the User has an injury, emergency or high concern incident the User can press their wearable emergency pendant, the emergency button on their smart health hub, the emergency button on the Addison device screen, or the User can use say Addison—HELP or Addison—Emergency to summon a 24/7 emergency response connection to the monitoring facility. If any method of pendant, smart hub button, voice or touch is used to initiate an emergency response the Addison screen will display a CALLING EMERGENCY SERVICES graphic and Addison's voice will say "Calling emergency services, standby".

An emergency alert will be transmitted to the monitoring station software and an alert will be sent to care circle responsible party apps and an IVR call will be made to the responsible party call list in sequence until a response is received from a third party using the IVR telephone interface. If an answering machine is received a message is left and the next responsible party IVR call is made. The first responsible party to acknowledge an IVR call (press 1 to acknowledge, etc.) will stop additional call tree actions. Concurrently a connection is established with an available monitoring operator who will announce themselves and speak to the User assessing the situation. If no User response is received OR the User reports an urgent condition the operator will transition to designated notifications to responders and responsible parties.

If the User reports an accidental emergency activation or reports no responder is verified as needed the operator will log the User response and no-action designation and will disconnect the call. The Addison console will return to idle screen. During any emergency involving notification the primary operator will remain in connection over the devices until a verified third party is on location with the User before disconnecting.

All Addison Assist options works by voice command from any screen or scene. The Addison touch buttons for emergency response, the telehealth service, customer service or Alexa on the Addison console can only be accessed by touching or using the voice command Addison Assist at which time the button will be displayed.

The Telehealth Service and Telemedicine

Addison can enable an option to connect a patient to a doctor over a secured, $3^{rd}$ party telehealth video engagement over the Addison device. The doctor can instruct the user to take a vital measurement and receive real time data which can be access through the proprietary Addison Connected Care platform, or through API call up to the Doctor's existing EMR.

The telehealth service is easily accessed by using touch or voice for the Addison Assist feature (button) on her home screen. If the User says or touches Addison Assist, Addison will transition to display options of which one is the telehealth service. Once the telehealth service option is presented the User initiates a call to the telehealth service by either touching the telehealth service button or using voice and saying Addison (her tablet will turn green to show she's listening) connect to the telehealth service, or other optional programmed request phrase.

Addison will acknowledge the command by saying "okay, calling the telehealth service" and a designated graphic will be displayed during the call indicating CONNECTING. Once the call is answered the graphic will display CONNECTED TO THE TELEHEALTH SERVICE and the telehealth service connection is established, or a help desk responds to establish a call at a scheduled time.

If a call cannot be completed a message will be displayed—WE'RE SORRY CALL FAILED—PLEASE DIAL 833-ECG-LIFE AND SELECT OPTION (numerical value) FROM YOUR PERSONAL PHONE TO CONTACT THE TELEHEALTH SERVICE.

If a call screen is stuck or hung up if the User delivers the verbal Addison Stop command any existing call will disconnect and the scene will transition back to Addison's idle state.

Contacting Customer Service.

If the User says Addison Assist from any screen or if the User presses the Addison Assist button in the upper right area of her console screen Addison will transition to display the available assist options (emergency button, the telehealth service, customer service or Alexa). If the User presses the Customer Service button or says Addison, Customer Service from the Addison Assist screen a duplex telephony call will be made to the ECG customer service department. A graphical message will indicate Calling Customer Service and once connected the message will transition to Connected. The ECG operator will engage the User to address their technical support needs. If the call appears to be longer than a few minutes the operator will be trained to request an immediate call back on the User's personal phone.

If a call cannot be completed a message will be displayed—WE'RE SORRY CALL FAILED—PLEASE DIAL 833-ECG-LIFE AND SELECT OPTION X FROM YOUR PERSONAL PHONE TO CONTACT THE TELEHEALTH SERVICE. Note—if an operator is not available, we want to work through our phone system to spot caller ID on unanswered calls and get back to the User. If the User reaches a voicemail system, they will leave a message and the call should disconnect. If a call screen is stuck or hung up if the User delivers the verbal Addison Stop command any existing call will disconnect and the scene will transition back to Addison's idle state.

Physical Therapy.

The Addison platform allows over 200 PT reminders and demonstrations, which can be schedule daily or on any intervals, 7 days a week. Addison will provide the reminder and demonstration if the customer has a specific routine to complete for a specific strength exercise, stretch and/or physical therapy routine that has been selected from the drop-down menus during the ordering process.

In addition to reminders, the Addison system will view, monitor and evaluate User biomechanical performance and feedback such as verification of compliance and, as an example, increased range of motion metrics. If a scheduled reminder has been programmed into the Addison Platform for a particular User, upon the designated time to alert the User the Addison console will sound an alert, present a graphical alarm image on the display screen with animation effects with text that says Physical Therapy Reminder and a button that says—Alarm Off. The audible alert sound should be attention grabbing but not irritating and should reflect a frequency range which can be detected by an average 80-year-old patient with mild to moderate hearing loss.

If the alert is acknowledged by the User by speaking the command "Addison . . . Alarm Off" or by pressing the button that indicates Alarm Off, the display alarm graphic will stop animation effects and the audible alert will stop and the display screen will transition to Addison speaking while concurrently displaying her words in the real time speech text box at bottom of screen. Addison will say User's name to address them with a permission request such as "Ms. Caroline, I have a message for you, are you ready to hear it?" and Addison will display buttons that indicate YES or NO and her tablet will display green and Addison listens for a response. If the User presses NO the PT reminder will be snoozed (delayed) and Addison will announce-"okay, I understand you're not ready for your Physical Therapy Routine now, I will remind you again in [default value] minutes. After [default or selected value] minutes has passed, the Addison system will repeat the alarm and will allow the default or selected value number of subsequent snooze cycles.

If the User does not respond to a Physical Therapy reminder alert, the alert will continue to audibly sound and display the customer reminder animation for the duration of the designated or default value selected at the time the system was ordered, or according to the last User account update that occurred if the original value was changed.

If the designated number of repeat alerts does not receive a response from the User, the system will transmit a PT failure alert to the monitoring facility software and deposit the alert in the company database and update any designated $3^{rd}$ party provider and caregiver portal and transmit an alert to any or all designated responsible parties within the care circle on their ECG android or iOS device. If the User responds by voice or press of YES button to a PT reminder the alert will be silenced, the reminder animation graphic will stop and vacate the screen. The display will present the scheduled PT routine to perform, and Addison will announce, "okay, it's time for you to perform your chair stand exercise (as an example . . . several Addison PT demo routines exist).

Addison will say "please touch or say READY when you are ready for me to demonstrate your physical therapy routine so you can follow along with me. You can also say tutorial if you want me to demonstrate the routine in advance to help you prepare."

If the User opts to for a tutorial Addison will perform an on-screen demonstration. Once the tutorial is completed Addison will repeat—"please touch or say READY when you are ready to begin your physical therapy routine. Once you've completed the routine say Addison—DONE or press the done button and I will document your accomplishment!"

Once the User says READY the Addison system begins the Avatar PT routine demonstration. The User is expected to follow along. If the User does not say READY after 5 minutes Addison will ask—"Are you almost ready to begin your Physical Therapy? If the User says yes Addison will standby and wait for the Ready command. Addison will repeat the question if the User has not started the routine a total of 3 times, 5 minutes apart. If the User has not given the READY command after 15 minutes Addison will log and transmit a non-PT adherence notice to the clinical portal, will log the event in the central station database and will transmit a PT non-adherence message to the care circle apps.

If the User says READY Addison will say—"okay, let's begin" and will demonstrate rehabilitation routines and repeat them including left and right if routine is so defined, the designated number of repetitions selected in the order architecture. If the User does not say DONE Addison will repeat the routines until the User says DONE. If after 30 minutes the User does not say DONE Addison will say—"I did not receive a response that you were DONE and will log this session as incomplete" and the Addison system will report a PT non-adherence alert as formally described to portal, care circle apps and central station and will return to her home screen.

If the User acknowledges completion of the physical therapy session by providing the Addison DONE response by either touch or voice, Addison will provide one of the pre-programmed positive alternating acknowledgements provided by her platform such as—"I understand you've completed the routine. This is good news and you're making great progress. I will log your performance in your health record. Congratulations!" etc. etc., and the system will report the completed routine to the central station database, the care circle platform and the clinical portal. In future generations the depth of field camera will be used to monitor and verify patient compliance and performance. Addison will provide an alignment box and demonstration to help position User in proper location for conducting PT routines and exercises. As the User follows Addison in the routines the camera uses skeletal tracking to measure duration, repetitions, and range of motion, reporting to User and clinical portal key performance metrics. For instance, if the User has had a shoulder procedure and is required to spider walk their hand up the wall to increase arm range of motion, Addison will note the continual increases to range of motion over time, or indications of stagnant performance or decline, and will report to the clinical portal accordingly.

The Addison system will schedule times with the User for a PT routine to assess fall risk, gait and balance. Addison will demonstrate User placement and walk test. EI-Walking four steps left to right in front of Addison console, turning and returning 4 steps, repeating this action until Addison says—"okay, stop, I've got your measurements". During the walk test period Addison will be measuring key indications including inverted pendulum swing, linear gait velocity, stride length, time in swing, time in double support, cadence and excursions from center of mass. Addison will then compare these measurements to a Fall Risk Screening Software module and will translate the assessment data into a user consultation to explain the results and fall risk score to the User using graphical and animation presentations.

The results of each walk test will be updated in the clinical portal where current results and prior trends can be examined with the more granular measurements. Alerts will be set for significant changes to various gait parameters and fall risk indicators to provide alerts for significant changes and out of threshold notifications. Certain anomalies discovered such as toe-drop can produce an auto-rehabilitation routine to improve results that are non-invasive and low User impact, such as exercises to strengthen muscles such as anterior tibialis by sitting in a chair, elevating your leg off the floor, and pretending to draw each letter of the alphabet with your elevated leg and toes. Incorporating the ability to Addison to suggest low impact, low risk routines which can be added by the user will be valuable in the future. Addison can capture fall risk assessments passively by taking snapshots of gait periodically as User moves about their interior living areas. The system can monitor response to a prescribed care plan for changes to medication routines and then provides ongoing monitoring for indications of instability, sluggishness and indications of an adverse drug reaction from the new medication.

Depth of Field Cameras and Addison software are also able to monitor specific events and anomalies such as reduction in time or number of attempts rising from bed or a chair, coupling these measurements with additional information such as speed of response in Addison voice or touch console engagements, indications of slurred or slower speech, or other indications integrated with learning algorithms to improve trend analysis and patient response, status and evaluation. The system can further be programmed to monitor for additional anomalies and measurements of more specific details such as sideward trunk lean, circumduction, retropulsion, festination, freezing gait, coxalgia gait, steppage gait, etc. In studies ⅔rds of indications of gait problems and falls risk was neurological and nearly half non-neurological. There is significant overlap of causes in both areas. Gait is as significant a predictor of looming mortalities as assessing all chronic illnesses combined. Addison can identify a variety of cognitive disorders and orthopedic issues and alerts can be applied to expedite more accurate treatment responses, use of orthotics, rehabilitation, pharmacology changes and dramatic improvements in outcomes, risk reduction, improved quality of life and functional independence.

Gamification Routines.

These are acknowledgements as well as reinforcements and encouragement based on details such as number of days compliant, to provide support for patients and users. Example—"This is great Ms. Caroline; you've been on track with medications for 22 days in a row!" Certain routines can be coupled with rewards such as "Ms. Caroline, if you stay on track with your care plan and medications for 9 more days, you'll add a new room to my home or you'll unlock a new outfit for me or you'll win a gift card!" We have examined the idea of patient rewards such as gift or meal cards or access to services, as well as Addison feature's updates to encourage User buy-in to increasing treatment adherence while being excited about the process. Early routines have been designed and prototyped to be simple emotionally and psychologically stimulating acknowledgments and encouragements which are added to the end of successful Vitals readings and Medication Reminder routines. Simple updates to this process are adding trend charts, Addison applauding or showing a new routine, unlocking a feature, or simulating fireworks or balloons released in the scene.

Addison is designed to incorporate existing games for mental stimulation and entertainment accessed from within the Addison scene where Addison can present the opening of the game and provide a short tutorial about using the game or building enthusiasm for using it.

Addison AI algorithms.

Machine learning algorithms and training software is used to access daily living data, to observe behavior, to measure the effects of health care or fitness engagements, to measure and compel behavioral change, to improve treatment adherence, to early identify health variations and anomalies, and to understand the mental and physical state of our customer in order to design the most effective ways to treat them. Addison is designed to identify ineffective treatment protocols, to identify trends and dangers in pharmacology, to deliver faster feedback in clinical trials, and to spotlight the most effective therapeutic methods for accelerating better mental and physical health outcomes.

General intelligence analytics include comparing user data including the patient's location, age, gender, preexisting health conditions, providers, medications and/or vitals readings, with voice assessment, biomechanical data, facial and speech recognition, countenance, general activity behaviors and mental and physical health feedback. These data points are indexed and evaluated along with change inputs to the user care plan, non-adherence indicators, adherence indicators, dosing data, identified reactions to new medications, number of medications, responses to health surveys and interactive assessments, events such as falls, and variable changes in trends and data. For example, did the patient walk slower, sleep more or less, did general activity patterns change, did their voice and countenance change, did their speed of response to reminders or interactive conversations change, did they access memory support features more frequently because they indicate memory loss, etc.?

Care Circle Apps.

The Care Circle app is currently provided as an iOS or Android app. Push notifications are sent to the app for non-adherence alerts, threshold alerts, emergency calls, and system low batteries for console, smart hub or pendant. The Care Circle user is also able to use a geolocation feature to identify the whereabouts of the User on-demand in real time. The geolocation feature is provided by our mobile device when associated with an Addison device.

Care Circle users can store multiple users in the app using their device ID numbers, can add a profile photograph for personalization, as well as view recent alerts for nonadherence, threshold, or recent vitals history. Care Circle connectivity is a key feature of the Addison suite of products. As defined within the specification numerous alerts and notifications transmit messages via SMS or text push notification to the app. The Care Circle app also allows the Care Circle member to record and transmit a voice message or text message to the Addison system.

Recorded messages are a unique and valuable feature for being able to transmit a specific user a message or provide the option to send a uniform message to all Addison in a Care network. Example, 120 consoles are installed at an Independent Living Facility and there is a food recall, extreme weather alert or power outage. Administrators of the Care Circle can broadcast messages with reassurance or instructions to the entire population and/or a specific message to an individual who may have special needs of circumstances.

Multiuser Service.

Addison is capable of monitoring, managing, and supporting multiple users from a single Addison device, or console. Addison can be programmed to call out and message two or more users personally for vitals, medication, rehab, mental health or health survey routines, who may be living in the same household. Devices are uniquely labeled, or color coded to associate them to a designated patient or users. Care plan personalization and engagement uses facial recognition and security features to share the proper care plan directives and feedback associated with the proper user.

What is claimed is:

1. An intelligent secure networked health messaging system configured by at least one processor to execute instructions stored in memory, the system comprising:
   a data retention system and a health analytics system, the health analytics system performing asynchronous processing with a patient's computing device and the health analytics system communicatively coupled to a deep neural network, the data retention system and the health analytics system coupled to the deep neural network configured as an isolated sub-system in secure isolation from a remainder of the intelligent secure networked health messaging system via one of a security protocol or layer;
   a web services layer providing access to the data retention and the health analytics system;
   a batching service, wherein an application server layer transmits a request to the web services layer for data, the request processed by the batching service asynchronously to a patient-facing application to reduce latency in data display and storage and to update operations of the patient-facing application;
   the application server layer including a data corridor established between the application server layer and the patient's computing device that:
      provides the patient-facing application that accesses the data retention system, the health analytics system, and the deep neural network through the web services layer;
      performs processing based on patient interaction with the patient-facing application, the patient-facing application configured to execute instructions including transmitting an interactive conversational patient interface to the patient's computing device;

the deep neural network configured to:
receive a first input at an input layer;
process the first input at one or more hidden layers;
generate a first output;
transmit the first output to an output layer;
provide the first output to the patient-facing application; and
provide the first output to the interactive conversational patient interface;
the patient-facing application with the interactive conversational patient interface converting the first output received by the patient's computing device into an audio file using a cloud-based text-to-speech application capable of being integrated into a web browser based avatar, the avatar being displayed on a display screen within the web browser of the patient's computing device as a three-dimensional electronic image of a human caregiver for a human patient, further comprising the three-dimensional electronic image of the human caregiver providing step-by-step verbal healthcare instructions to the human patient, monitoring a response from the human patient, and providing healthcare advice to the human patient based on the first output.

2. The intelligent secure networked health messaging system of claim 1, further comprising the first output generating a first outcome.

3. The intelligent secure networked health messaging system of claim 2, further comprising the first outcome being transmitted to the input layer, processing the first outcome by the one or more hidden layers, generating a second output, transmitting the second output to the output layer, providing the second output to the patient-facing application and the second output generating a second outcome.

4. The intelligent secure networked health messaging system of claim 3, further comprising the second outcome being transmitted to the input layer.

5. The intelligent secure networked health messaging system of claim 1, further comprising the first output including any of a clinically relevant care plan, a reminder, an alert, or a survey.

6. The intelligent secure networked health messaging system of claim 1, further comprising an outcome including any of a biometric parameter, a biometric parameter out of a predetermined threshold, a response to a survey, medication compliance information, an indicator of daily activity, an indicator of mood, or an indicator of stress.

7. The intelligent secure networked health messaging system of claim 1, further comprising the processing by the one or more hidden layers including using voice, speech, and computer video inputs to analyze signs of changes in health and behavioral status including but not limited to stress, anger, change in speech cadence, slurred speech or coughing.

8. The intelligent secure networked health messaging system of claim 7, further comprising the processing determining changes in the health and behavioral status including but not limited to anger, substance use, lack of sleep, stress, early onset of dementia or Alzheimer's disease, an adverse reaction to a medication, a stroke, Parkinson's disease, an increased risk of falling, or a lack of balance.

9. The intelligent secure networked health messaging system of claim 1, further comprising the interactive conversational patient interface configured to mirror an interior environment.

10. The intelligent secure networked health messaging system of claim 9, the mirrored interior environment including a realistic depiction of a fireplace that turns on when a temperature is below a certain threshold.

11. The intelligent secure networked health messaging system of claim 9, the mirrored interior environment including a depiction of the patient's favorite color on an item in the patient's home.

12. The intelligent secure networked health messaging system of claim 9, the mirrored interior environment including a depiction of the patient's favorite art style on an item in the patient's home.

13. The intelligent secure networked health messaging system of claim 9, the mirrored interior environment including a depiction of holiday and religious celebration items in the patient's home.

14. The intelligent secure networked health messaging system of claim 9, the mirrored interior environment including a depiction of the patient's favorite animals or pets in the patient's home.

15. The intelligent secure networked health messaging system of claim 9, the mirrored interior environment including a depiction of interactable objects that respond when touched in the patient's home.

16. The intelligent secure networked health messaging system of claim 15, the mirrored interior environment including a depiction of interactable objects including any of a piano, radio, bird feeder, plant, animal, wind chime, teacup, or vase that responds when touched in the patient's home.

17. The intelligent secure networked health messaging system of claim 15, the mirrored interior environment including a depiction of interactable objects including a book that can be opened and read via touch or voice.

18. The intelligent secure networked health messaging system of claim 9, the mirrored interior environment including a depiction of a patient's hobby in the patient's home.

19. The intelligent secure networked health messaging system of claim 18, the mirrored interior environment including a depiction of the patient's hobby in the patient's home, the hobby being skiing.

20. The intelligent secure networked health messaging system of claim 18, the mirrored interior environment including a depiction of the patient's hobby in the patient's home, the hobby being snowboarding.

* * * * *